(12) United States Patent
Cappelli et al.

(10) Patent No.: US 7,906,551 B2
(45) Date of Patent: Mar. 15, 2011

(54) 3-SUBSTITUTED-1,5-DIARLY-2-ALKYL-PYRROLES HIGHLY SELECTIVE AND ORALLY EFFECTIVE COX-2 INHIBITORS

(75) Inventors: Andrea Cappelli, Civitella Marittima (IT); Maurizio Anzini, Pianella (IT); Mariangela Biava, Rome (IT); Francesco Makovec, Lesmo (IT); Antonio Giordani, Pavia (IT); Gianfranco Caselli, Milan (IT); Lucio Claudio Rovati, Monza (IT)

(73) Assignee: Rottapharm S.p.A., Milan (IT)

( * ) Notice: Subject to any disclaimer, the term of this patent is extended or adjusted under 35 U.S.C. 154(b) by 0 days.

(21) Appl. No.: 12/375,650

(22) PCT Filed: Aug. 3, 2006

(86) PCT No.: PCT/EP2006/065011
§ 371 (c)(1),
(2), (4) Date: May 6, 2009

(87) PCT Pub. No.: WO2008/014821
PCT Pub. Date: Feb. 7, 2008

(65) Prior Publication Data
US 2009/0264500 A1 Oct. 22, 2009

(51) Int. Cl.
*A61K 31/40* (2006.01)
*C07D 207/30* (2006.01)
(52) U.S. Cl. .................. 514/427; 548/561; 548/562
(58) Field of Classification Search .................. 514/427; 548/561, 562
See application file for complete search history.

(56) References Cited

FOREIGN PATENT DOCUMENTS

| DE | 2 261 965 A1 | 6/1973 |
|---|---|---|
| EP | 0323841 A2 | 12/1989 |
| EP | 0 799 823 A1 | 10/1997 |
| WO | 98/25896 A1 | 6/1998 |

OTHER PUBLICATIONS

Ish K. Khanna, et al, "1,2-Diarylpyrroles As Potent and Selective Inhibitors of Cyclooxygenase-2", Journal of Medicinal Chemistry, American Chemical Society, 1997, pp. 1619-1633, vol. 40, No. 11, XP-002059990.
Mariangela Biava, et al, "1,5-Diarylpyrrole-3-Acetic Acids and Esters As Novel Classes of Potent and Highly Selective Cyclooxygenase-2 Inhibitors", Journal of Medicinal Chemistry, Dec. 4, 2005, p. 3428-3432, vol. 48, No. 9, XP-002446244.
F. Cerreto, et al, "Studies on Anti-Candida Agents With a Pyrrole Moiety. Synthesis and Microbiological Activity of Some 3-Aminomethyl-1,5-Diaryl-2-Methyl-Pyrrole Derivatives", European Journal Medicinal Chemistry, Oct. 1992, pp. 701-708, vol. 27, No. 7, XP-002446245.

Jean-Michel Dogn, et al. Journal of Medicinal Chemistry. Adverse Cardiovascular Effects of the Coxibs. J. Med. Chem., 2005, 48 (7), 2251-2257, 2005.
J. Scott Sawyer, et al. Synthesis and activity of new aryl- and heteroaryl-substituted 5,6-dihydro-4H-pyrrolo[1,2-b]pyrazole inhibitors of the transforming growth factor-β type I receptor kinase domain Bioorganic & Medicinal Chemistry Letters 14 (2004) 3581-3584.
Candida F. Pereira, et al. Induction of cyclooxygenase-2 expression during HIV-1- infected monocyte-derived macrophage and human brain microvascular endothelial cell interactions, Journal of Leukocyte Biology, vol. 68, Sep. 2000, p. 423.
Jiuxiang Zhu. et al. From the Cyclooxygenase-2 Inhibitor Celecoxib to a Novel Class of 3-Phosphoinositide-Dependent Protein Kinase-1 Inhibitors, Cancer Research, vol. 64, pp. 4309-4318, Jun. 15, 2004.
G.E. Leighton et al, k-Opioid agonists produce antinociception after i.v. and i.c.v. but not intrathecal administration in the rat; Br. J. Pharmacol. (1988), 93, pp. 553-560.
Giulio Maria Pasinetti, et al, Cyclooxygenase and Alzheimer's disease: implications for preventive initiatives to slow the progression of clinical dementia, Archives of Gerontology and Geriatrics 33 (2001) pp. 13-28.
Robert S. Bresalier, MD. et al. Cardiovascular Events Associated with Rofecoxib in a Colorectal Adenoma Chemoprevention Trial, New England Journal Medicine, 2005, vol. 352, 2005 on Feb. 15, 2005.

(Continued)

*Primary Examiner* — Kamal A Saeed
*Assistant Examiner* — Kristin Bianchi
(74) *Attorney, Agent, or Firm* — Sughrue Mion, PLLC

(57) ABSTRACT

This invention relates to 3-substituted-1,5-diaryl-2-alkyl-pyrroles of Formula I, pharmaceutical compositions containing them, and to their use for the pharmacological treatment of pain and COX-2 over-activation associated disorders. Compounds of this invention are new pyrrole derivatives bearing in position -3 of the pyrrole ring, several variously functionalized, not aliphatic, side chains which confer to the compounds a relevant COX-2 potency and selectivity along with a remarkable oral efficacy. Phenyl rings in position -1 and -5 are variously substituted, but compounds of particular interest are those substituted in position -5 with 4-methylsulphonyl-phenyl or with 4-aminosulphonyl-phenyl groups.

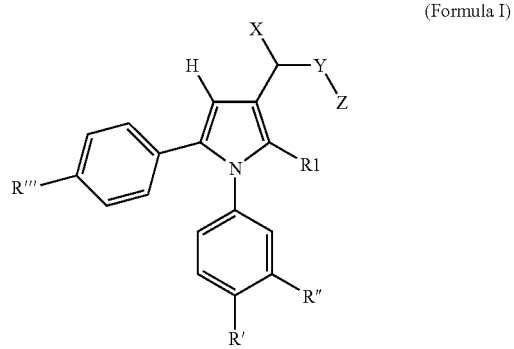

(Formula I)

26 Claims, No Drawings

OTHER PUBLICATIONS

F. Corelli et al. Agenti Antiinfiammatori Non-Steroidei, IL Farmaco 1988(43): 251.

Rosario Sanchez-Pernaute Selective COX-2 inhibition prevents progressive dopamine neuron degeneration in a rat model of Parkinson's disease, Journal of Neuroinflammation, 2004,1:6.

Current Drug Targets—Inflammation & Allergy, vol. 4, No. 3, 2005. p. 5.

S.T. Meller et al., The possible role of Glia in Nociceptive Processing and Hyperalgesia in the Spinal Cord of the Rat. Neuoropharmacology, vol. 33 No. 11, pp. 1471-1478, 1994.

Lowell O. Randall et al. A method for measurement of analgesic activity on inflamed tissue, Arch. Int. Pharmacodyn cxl, No. 4, 1957 pp. 111 409.

Paul F. Jackson et al. Pyridinylimidazole Based p38 MAP Kinase Inhibitors, Current Topics in Medicinal Chemistry, 2002, vol. 2, pp. 1011-1020.

Hermann Stetter, Angewandte Chemie, International Edition in English, vol. 15, No. 11, 1976 pp. 639-712.

Sean D. Hurley et al, Review, Cyclooxygenase Inhibition as a Strategy to Ameliorate Brain Injury, Journal of Neurotrauma, vol. 19 No. 1, 2002.

P.N. Pompl. et al, A therapeutic role for cyclooxgenase-2 inhibitors in a transgenic mouse model of amyotrophic lateral sclerosis, Faseb J. 2003, 17 vol. 6. pp. 725.

Basilia Zingarelli, The inhibitory effects of mercaptoalkylguanidines on cyclo-oxygenase activity, British Journal of Pharmacology (1997) vol. 120, pp. 357-366.

G Stefancich, Agenti Antiinfiammatori Non-Steroidei, II Farmaco—Ed. Sc.—vol. 39, p. 752-753, 1984.

R Koster et al, Acetic acid for analgesic screening, 1959,18,412, Supplied by The British Library.

Weiping Qin, et al. Cyclooxygenase (COX)-2 and COX-1 Potentiate β-Amyloid Peptide Generation through Mechanisms That Involve γ-Secretase Activity, The Journal of biological chemistry 2003 By The American Society for Biochemistry and Molecular Biology. Inc, vol. 278, No. 51. pp. 50970-50977. 2003.

3-SUBSTITUTED-1,5-DIARLY-2-ALKYL-PYRROLES HIGHLY SELECTIVE AND ORALLY EFFECTIVE COX-2 INHIBITORS

This invention relates to 3-substituted-1,5-diaryl-2-alkyl-pyrroles derivatives and pharmaceutical compositions containing such compounds. More specifically it relates to compounds acting as selective COX-2 inhibitors, orally effective, and as such useful for the pharmacological treatment of pain and COX-2 over-activation associated disorders.

BACKGROUND

Cycloxygenase (COX), or prostaglandin $H_2$ ($PGH_2$) synthase is the key enzyme able to catalyze the formation of prostaglandins from arachidonic acid. $PGH_2$, the product of COX, is the common precursor for the biosynthesis of prostaglandins, prostacyclins and thromboxanes. COX is the well known target of nonsteroidal anti-inflammatory drugs (NSAIDs), which have been used for about one century as first line therapy for relieving inflammation and pain associated with a number of arthritic conditions. Prostaglandins ($PGD_2$, $PGI_2$, $PGE_2$, $PGF_{2\alpha}$) have various effects on mammalian physiology, in particular prostaglandin $E_2$ ($PGE_2$), which is the predominant eicosanoid detected in inflammation conditions, is an important mediator of pain, fever and other symptoms associated with inflammation. Accordingly, inhibition of the biosynthesis of prostaglandins has been a target for the therapeutic treatment of pain and inflammatory conditions for years. Main adverse-effect associated with the chronic usage of NSAIDs, is for a great part of the population, gastrointestinal irritation which can give rise to life threatening lesions and ulceration if the therapy is not interrupted. Another rather common adverse effect of NSAIDs is renal toxicity. An alternative to NSAIDs is the use of corticosteroids, however also in this case chronic use can result in severe side effects.

In the early 1990s it was demonstrated that COX exists as two distinct isoforms that catalyze the same reaction but differ in terms of regulation; in particular it was shown how COX-1 is constitutively expressed as a house keeping enzyme in almost all tissues, and is responsible for those physiological functions such as for example cytoprotection of the gastrointestinal tract, platelet aggregation, vascular tone. On the other hand, COX-2, the second isoform, was identified as an inducible enzyme, highly expressed in response to inter-leukin-1β (IL-1β) and other inflammatory stimuli. Thus, COX-2 was proposed as responsible for the production of prostaglandins associated with pain and inflammatory conditions. The expression of COX-2 is indeed regulated by a broad spectrum of mediators involved in inflammation in the most of tissues. Whereas lipopolysaccharide and proinflammatory cytokines (IL-1β, TNFα) can induce COX-2, glucocorticosteroids and interleukins-4, -13 and -10 inhibit the expression of this enzyme in response to an anti-inflammatory stimulus. Thus, several line of evidence supported the selective inhibition of COX-2 as a potentially powerful new mechanism for the treatment of the inflammatory related diseases and relief of acute pain, with a lower incidence of gastrointestinal-related adverse events compared with non-selective NSAIDs.

This led to a tremendous medicinal chemistry effort which gave rise in a few years to a plethora of compounds (including Rofecoxib, Celecoxib, Valdecoxib, Parecoxib and later Etoricoxib and Lumiracoxib) (Figure 1) endowed with different COX-1/COX-2 selectivity, and different pharmacokinetic and toxicological profiles.

Clinical trials with these compounds largely confirmed the effectiveness of the approach in the treatment of inflammatory disorders such as arthritis and for the management of acute pains in adults, as well as confirmed the expected safety of these drugs as far as gastrointestinal damages are concerned. Celecoxib and Rofecoxib were shown, in strict clinical trials, to cause a significantly lower incidence of upper gastrointestinal adverse effects (perforations and ulcers) in comparison to classical NSAIDs.

Whereas in the early 1990s COX-2 was regarded as an enzyme only connected with inflammatory diseases and pain, in the following years its involvement in other pathologies turned out.

Epidemiological studies highlighted at the end of the 1990's how the risk of developing Alzheimer's disease (AD) was significantly reduced among users of NSAIDs. Recently, several lines of evidence established the role of COX-2 in AD (Arch. Gerontol. Geriatr., 2001, 33, 13-28). It was shown how in AD COX-2 is up regulated in brain areas related to memory (hippocampus, cortex), with the amount of COX-2 correlating with the amount of deposition of β-amyloid protein in the neuritic plaques. Several works demonstrated how this correlation between COX-2 activation and deposition of β-amyloid is supported by a well defined mechanism. In a transgenic mouse model of Alzheimer's disease it was shown that COX is influencing Amyloid-β peptide generation through a mechanism that involve $PGE_2$ mediated potentiation of γ-secretase activity (J. Biol. Chem., 2003, 278, 51, 50970). In addition it was reported that in astrocytes β-amyloid peptide 25-35 induces COX-2 mRNA and protein synthesis with subsequent release of $PGE_2$ by the astrocyte. This could give rise to a self-amplifying loop where $PGE_2$ is potentiating Amyloid-β peptide generation, which in turn potentiate $PGE_2$ production. Elevation of COX-2 expression in hippocampal neurons during the early phase of AD (mild dementia) is considered to favour the later neurodegenerative process. Further evidences suggest that COX-2 derived prostanoids potentiate glutamate excitotoxicity, thereby accelerating neurodegeneration. Thus, accumulating findings are showing how COX-2 inhibitors can prevent AD and even counteract the progression of the disease (MG Giovannini, Experimental brain inflammation and neurode-generation as model of Alzheimer's disease: protective effects of selective COX-2 inhibitors).

Many brain disorders such as Parkinson's disease (PD), amyotrophic lateral sclerosis (ALS), Huntington disease, HIV induced dementia and head trauma are associated with inflammation. Microglia and astrocytes act as immune cells in the inflamed brain, and especially microglia contribute to the onset of inflammation in many brain disease by producing proinflammatory mediators, among them prostaglandins.

A microglia reaction associated with up-regulation of COX-2 along with iNOS has been suggested to play an important role in dopaminergic neuron loss in PD (J. of Neuroinflammation 2004, 1:6; J. of Neuroinflammation 2006, 3:6), and selective COX-2 inhibition has been shown to prevent progressive degeneration in a rat model of Parkinson's disease.

Recent studies pointed out the presence of inflammatory markers in affected neural tissues of ALS patients, and macrophages in the ALS spinal cord highlighted strong expression of COX-2. Further studies suggested that COX-2 could promote motor neuron loss in rodent models of ALS while COX-2 inhibitors can significantly delay the onset of motor dysfunction in a transgenic mouse model of ALS (FASEB J., 2003, 17, 6, 725).

Human immunodeficiency virus type-1 (HIV-1)-associated dementia (HAD) is a neurodegenerative disease characterized by HIV infection and replication in brain tissue. HIV infected monocytes overexpress COX-2 as demonstrated both in vitro and in vivo models (J. Leukoc. Biol., 2000, 68, 3 423). Also in this case overproduction of inflammatory prostaglandins trigger or contribute to the triggering of those inflammation-mediated neurodegenerative processes which in turn give rise to neuronal loss (Current Drug Targets Inflamm. Allergy, 2005, 3, 335).

Among major targets for COX-2 inhibition, COX-2 expression by vulnerable neurons and by microglia which in turn give rise to the neuroinflammatory response (J. Neurotrauma, 2002, 19, 1). have been identified for a potential treatment of brain injury. Evidence suggests that using an appropriate treatment paradigm, COX-2 inhibition can impact these three targets and thus will be a useful, ameliorative adjunct in the treatment of most forms of brain injuries.

The capacity of NASIDs, such as Aspirin and Sulindac, to reduce colorectal cancer mortality was highlighted by clinical studies during the 1980s. Later the clinical efficacy of COX-2 inhibitors in cancer chemoprevention was demonstrated by randomised studies in patients with a precancerous condition. An involvement of COX-2 in several forms of solid tumors is supported by its over-expression in gastric, hepatic, esophageal, pancreatic, head and neck, colorectal, breast, bladder, skin and lung cancers when compared with non-malignant controls.

In five large-size clinical trials involving the COX-2 inhibitors: Celecoxib, Rofecoxib, Valdecoxib was highlighted an increased incidence of myocardial infarction and stroke. In September 2004 Rofecoxib was voluntarily withdrawn from the market for increased cardiovascular risk and the same happened in April 2005, with Valdecoxib. Though, incidence of adverse cardiovascular events with Rofecoxib is quite evident, especially considering the results of the VIGOR trial (Vioxx Gastrointestinal Outcomes Research; P. Juni, Risk of cardiovascular events and Rofecoxib: cumulative meta-analysis, Lancet, 2004, 364, 2021), where there was a five-fold increase in the incidence of acute myocardial infarction in the Rofecoxib arm of the trial when compared with the Naproxen arm, clinical results of trials dealing with the same adverse-effect didn't highlight any significant difference when Celecoxib was compared to classical NSAIDs. In order to explain this unexpected cardiovascular toxicity, it was speculated that selective COX-2 inhibitors may block the production of prostacyclin (antithrombotic) and leave thromboxane (prothrombotic) generation unaffected. This explanation, which could suggest the increased cardiovascular risk is a feature of the whole class of selective COX-2 inhibitors, is supported by the recent findings that COX-2 is constitutively expressed by some tissues, such as vascular endothelium and kidney. According to this explanation, selective COX-2 inhibitors cannot inhibit COX-1, constitutive within the platelets and associated with the production of thromboxane $A_2$ ($TXA_2$; a potent inducer of platelet aggregation and vasoconstriction), but can inhibit the endothelial COX-2 which is producing prostacyclin, that inhibits platelet aggregation and give rise to potent vascular smooth muscle dilation. This selective inhibition of the vasodilatation/anti-aggregation promoter without concomitant inhibition of the vasoconstrictor/pro-aggregant stimulus $TXA_2$ (as usually happens with non selective NSAIDs) should explain the increased evidence of cardiovascular risk when comparing selective COX-2 inhibitors with classical NSAIDs. The same explanation could also address the potential renal toxicity attributed to the class of COX-2 inhibitors.

This hypothesis is well matching with the first clinical data where the less selective Celecoxib displayed no cardiovascular adverse event, however is not matching with a second set of clinical data coming from a study aimed at establishing whether Celecoxib could treat AD, where incidence of heart attack was four times higher in the treated group in comparison to placebo (JMC, 2005, 2251-2257).

Also in contradiction with this hypothesis is the fact that for the highly COX-2 selective inhibitors Etoricoxib and Lumiracoxib, the evidences for cardiovascular adverse events, in specifically designed clinical trials, seems to be more ambiguous in comparison to the ones produced for Rofecoxib.

Looking at the overall available body of data concerning the relationships between selective COX-2 inhibitors and cardiovascular events at least conflicting evidence could be recognized. The cardiovascular risks of COX-2 inhibitors appear heterogeneous, influenced not only by the drug class, but also by the individual structure of the drug, and by the dosage (Expt. Opin. Drug Saf. 2005, 4, 6, 1005).

Taking into account the structures of the best known inhibitors (Figure 1) it could be recognized that Rofecoxib, Celecoxib and Valdecoxib closely share the diaryl substituted heterocyclic moiety while Etoricoxib for some extent and for a larger extent Lumiracoxib are progressively differentiating from this common simple scaffold.

Diversity in the chemical structure of COX-2 inhibitors not only could account for differences in the ADME profiles (i.e.: Celecoxib which is extremely high lipophilic is sequestered in body fat while Lumiracoxib, due to the acetic moiety, reaches higher circulating concentration) which in turn may also reflect in a different cardiovascular impact, but also can influence pharmacological responses not mediated by COX-2 but due to other mechanisms.

For example, even in the quite homogeneous class of the diaryl-substituted heterocycles Celecoxib and Valdecoxib sharing the arylsulphonamide group with many carbonic anhydrase inhibitors, are able to reduce intraocular pressure (not COX-2 dependent effect) in glaucomatous rabbits, while Rofecoxib which has the methylsulphonyl group instead of the sulphonamide group, had no effect. Conversely, the sulphone group in the structure of Rofecoxib increases susceptibility of low-density lipoprotein to oxidative modifications, while Celecoxib had no effect (J. Med. Chem., 2005, 48, 2255). Diaryl-substituted heterocycles are suitable scaffolds for interaction with the ATP site of protein kinases. For example, Celecoxib induces apoptosis by a COX-2 independent mechanism (Cancer Research, 2004, 64, 4309) by blocking 3-phosphoinositide-dependent protein kinase-1 (PDK-1) which in turn activate Akt (Protein Kinase B) a kinase involved in cell cycling. These examples highlight how many different effects, not COX-2 dependent, can be found even in few related structures.

The above issues along with the previously mentioned conflicting body of clinical data regarding COX-2 inhibitors and adverse cardiac event, suggest that this side effect could be completely or in part structure related. Structural issues can also reflect in unfavourable ADME profiles and/or action through other mechanisms which could give rise to an higher or lower cardiovascular toxicity as a whole outcome.

These considerations indicated that there is still need for structurally diversified COX-2 inhibitors possibly able to overcome the safety issues highlighted with the first and second generation of this group of highly effective and useful drugs.

FIGURE 1

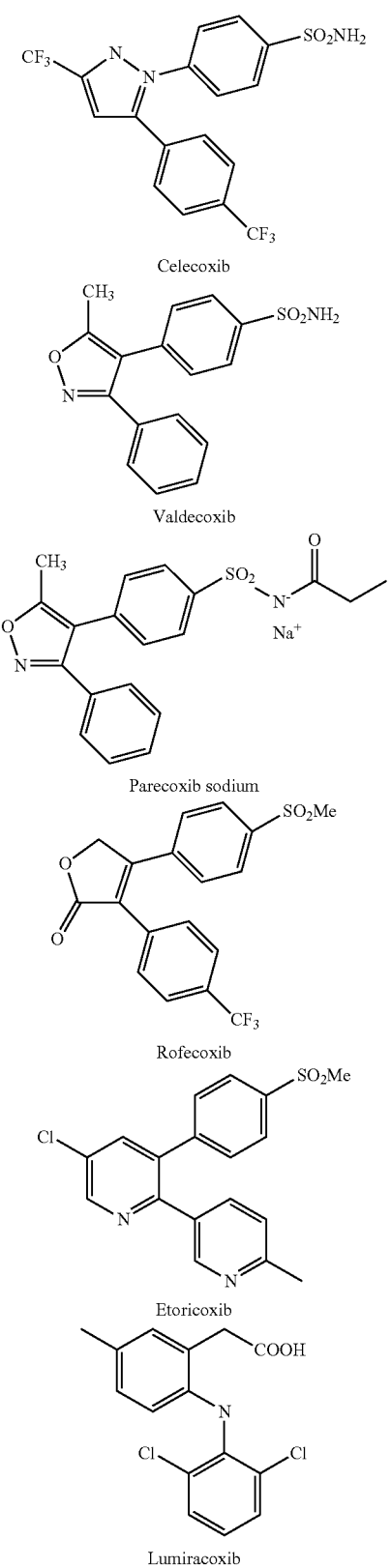

Celecoxib
Valdecoxib
Parecoxib sodium
Rofecoxib
Etoricoxib
Lumiracoxib

Looking at the structures in Figure 1, with exclusion of Etoricoxib and Lumiracoxib it could be recognized how diaryl-substituted penta-atomic heterocycles could be particularly well shaped for originating potent and selective COX-2 inhibitors. However, it was also above discussed how this pattern can be in addition well suited for interaction with the ATP site of kinases, for instance as reported for Celecoxib and PDK-1. In addition, the 1,2-diaryl substitution pattern can be recognized in a number of penta-atomic heterocycles, particularly imidazoles and pyrazoles, for example in the class of MAP kinase inhibitors (Current Topics in Medicinal Chemistry, 2002, 2, 1011; Bioorganic Medicinal Chemistry Letters, 2004, 3581). The too high lipophilic character of Celecoxib, which reflected in a drug with not completely favourable ADME characteristics, also suggested to avoid too lipophilic scaffolds.

In order to decrease the possibility of unwanted potentially not safe interaction with other targets (es. kinases) while selecting scaffolds with not too high lipophilicity, in order to optimize ADME characteristics, we preferred the pyrrole nucleus as the core heterocycle. The pyrrole nucleus as well as suitably substitutes pyrroles are moieties present in several natural and safe substances. This heterocycle is not particularly unstable from a metabolical standpoint, does not give rise to reactive intermediates by metabolic activation, is endowed of a suitable hydrophilicity. As drugs pyrroles have been described for various uses including treatment of inflammation (Il Farmaco, 1984, 756-80; where 1,5-diaryl-3-methyl-pyrroles are discussed), pain pharmacological treatment (DE 1972-2261965; where 1-aryl-2,5-dimethyl-3-aminomethyl-pyrroles are discussed as analgesics and antipyretic, for cardiovascular therapeutic treatment (EP 0323841, where 1-methylaryl-5-alkyl-2-substituted-pyrroles along with pyrazole and triazole are described as angiotensin II antagonists). 1,5-diaryl-2-methyl-3-aminomethyl-pyrroles have been described as antibacterial agents and anti-candida agents (F. Cerreto, Eur. J. Med. Chem. 1992, 27, 701; M. Scalzo, Il Farmaco, 1988, 43, 655). In the case of this pyrrole derivatives the presence of the aminomethyl group in position 3 is fundamental for the microbiological activity, while aromatic rings substitution pattern is modulating this activity. 1,5-Diaryl-pyrroles as selective COX-2 inhibitors have been described (WO98/25896); in this patent application, though the substitution of the aromatic rings in part is matching the corresponding one in this patent application, striking structural differences in the substitution of the pyrrole ring at position 2 and particularly at position 3 can be recognized between the two inventions. Synthetic preparation of the 1,2-diaryl-pyrroles has been reported by Stetter (H. Stetter, Angew. Chem. Int. Ed. Engl., 1976, 15, 639) and more recently by Khanna (I. K. Khanna, J. Med. Chem., 1997, 40, 1619).

The safety profile of Lumiracoxib along with its favourable ADME characteristics suggest how a proper functionalized side chain can modulate overall drug solubility and lipophilicity, as well as could limit undesirable interactions with possible targets other than COX-1/2. As the matter of fact, the first generation of COX-2 selective inhibitors is not represented by structures particularly functionalized, they are rather simple structures that if on one hand are able to achieve an high COX-1/COX-2 selectivity, on the other hand could potentially interact with several other targets.

Accordingly, increasing compound functionalization can be a means, for those cases where activity and COX-1/COX-2 selectivity is retained, to increase product safety by decreasing possible interactions with undesidered targets and/or properly modulating drug ADME characteristics.

1,5-Diarylpyrroles bearing side chains functionalized with carboxylate or related moieties have been reported previously. 1,5-Diarylpyrroles bearing in the position 2 the butanoic as well as the propanoic chains have been described (I. K. Khanna, mentioned above), these compounds however were found to be very week inhibitors of COX-2 both as esters and carboxylic acids independently upon the substitution pattern at the aromatic rings in positions-1 and -5. The presence of lipophilic substituents in the pyrrole position-3 give rise to potent COX-2 inhibitors when the substituent is an halogen atom or a trifluoromethylsulphonyl group. Introduction in position-3 of short side-chains such as an hydroxymethyl or a dimethylaminomethyl have been proved deleterious for COX-2 inhibitory activity (v.s.), while longer and more functionalized chains have not been yet reported.

SUMMARY OF THE INVENTION

The present invention provides a compound of the following Formula I,
Compound of Formula I:

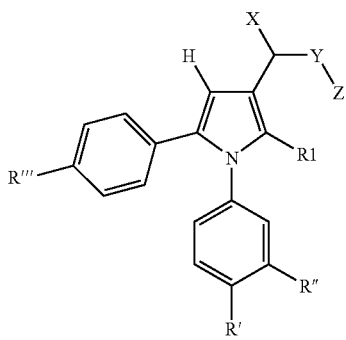

wherein:
- the substituent in position 1 of the pyrrole ring is a phenyl, substituted at meta and para positions, with R' and R" groups independently selected from: hydrogen, fluorine, chlorine, bromine, methyl, trifluoromethyl, methylsulphonyl (—SO$_2$Me), and aminosulphonyl (—SO$_2$NHR$_2$) where R$_2$ is defined below, provided that R' and R" are not simultaneously trifluoromethyl, methylsulphonyl, aminosulphonyl;
- the substituent R1 in position 2 of the pyrrole ring is methyl, ethyl, isopropyl, n-butyl, isobutyl;
- the substituent in the position 3 of the pyrrole ring is a two carbon atoms chain, wherein the groups X, Y, Z have the following meanings:
- X is independently selected from: hydrogen, hydroxy (—OH), alkoxy (—OR$_2$) wherein R$_2$ is an alkyl group as defined below;
- Y is independently selected from: a carbonyl group (C=O) or a methylene group (—CH$_2$—);
- Z is independently selected from: hydroxy (—OH), alkoxy (—OR$_3$), amino (—NH$_2$), alkylamino or arylamino (—NHR$_3$), dialkylamino or alkylarylamino (—NR$_2$R$_3$), alkylamido or arylamido (—NHCOR$_3$), dialkylamido or alkylarylamido (—NR$_2$COR$_3$), alkylcarboxyl or arylcarboxyl (—OCOR$_3$), alkyl or aryl carbonate (—O—CO—OR$_3$), alkyl or aryl carbamate (—NH—CO—OR$_3$ or —O—CO—NR$_2$R$_3$), ureido (—NH—CO—NHR$_3$), wherein R$_2$ and R$_3$ groups are as defined below, provided that:
- when Y is the C=O group and X is H, Z is not hydroxy;
- when Y is the C=O group, Z is alkoxy and X is H, R$_3$ is not methyl and ethyl;
- when Z is selected between alkylamido or arylamido (—NHCOR$_3$), dialkylamido or alkylarylamido (—NR$_2$COR$_3$), alkylcarboxyl or arylcarboxyl (—OCOR$_3$), alkyl or aryl carbonate (—O—CO—OR$_3$), alkyl or aryl carbamate (—NH—CO—OR$_3$ or —O—CO—NR$_2$R$_3$), ureido (—NH—CO—NHR$_3$), Y is a methylene group;
- when Z is selected between amino (—NH$_2$), alkylamino or arylamino (—NHR$_3$), dialkylamino or alkylarylamino (—NR$_2$R$_3$) Y is the CO group;
- the group R$_2$ is: methyl, ethyl, n-propyl, isopropyl, n-butyl, sec-butyl, iso-butyl;
- the group R$_3$ is: hydrogen, methyl, ethyl, n-propyl, isopropyl, n-butyl, sec-butyl, iso-butyl, benzyl (—CH$_2$Ar), 1-ethylaryl [—CH(Me)Ar] and aryl(Ar); provided that the R$_3$ group is not hydrogen when the Z group is selected between alkyl or aryl carbonate (—O—CO—OR$_3$) and alkyl or aryl carbamate (NH—CO—OR$_3$); the aryl group (Ar) is a phenyl, a substituted phenyl, a pentaatomic aromatic heterocycle independently selected from 2-thienyl, 3-thienyl, 2-furyl, 3-furyl, 2-pyrrolyl, 3-pyrrolyl, 3-isoxazolyl. For a substituted phenyl herein is intended a phenyl bearing one or two substituents independently selected from fluorine, chlorine, bromine, cyano, nitro, methyl and trifluoromethyl;
- the R''' group is independently selected form hydrogen, methylsulphonyl (—SO$_2$Me), and aminosulphonyl (—SO$_2$NHR$_2$), fluorine, chlorine, trifluoromethyl; provided that in each compound of formula I only one of the R''' and R' substituents is the methylsulphonyl or the aminosulphonyl group and R''' and R' are not simultaneously methylsulphonyl or aminosulphonyl.

When X is not hydrogen compounds of Formula I are chiral compounds, since the introduction of an hydroxyl or alkoxy group within the side chain give rise to an asymmetric centre; in this case compounds of Formula I can exist as individual enantiomers (S or R) or as mixture of such enantiomers. Enantiomers can also exist when Y is C=O and the Z group is the chiral sec-butyloxy group, in this case compounds of Formula I are chiral esters. In the case the Z group is a chiral amine such as —NHCH(Me)Ar, the compounds of Formula I are chiral amides. The present invention is also directed to both the enantiomers and their racemic mixtures or enriched mixtures of enantiomers of compounds of Formula I as chiral esters or amides. When the X group is an hydroxyl or alkoxy group, Y is carbonyl, and at the same time the Z group is a chiral ester or amine, compounds of formula I can exist both as diastereoisomers and enantiomers. The present invention also includes all the possible diastereoisomers and enantiomers of compounds of Formula I.

Compounds of Formula I are selective inhibitors of COX-2, and preferred compounds of this invention are orally active and safe COX-2 inhibitors. The compounds of the invention are useful for the treatment of COX-2 mediated disorders, including but not limited to: analgesic treatment of pain (for example postoperative pain, dental pain, muscular pain, pain resulting from cancer), treatment of inflammatory diseases such as arthritis, typically rheumatoid arthritis and osteoarthritis, asthma and inflammatory diseases of the respiratory tract, COPD, viral infection or serious allergic events, systemic lupus erythematosus, skin diseases such as eczema, psoriasis and dermatitis, premature labours, gastrointestinal serious inflammatory conditions such as inflammatory bowel disease (IBD), ulcerative colitis, Crohn's disease (CD), irritable bowel syndrome (IBS), post operative inflammatory complications. In addition compounds of the invention will be useful in the treatment of neurodegenerative diseases, involving COX-2 over-activation, such as Alzheimer's disease (AD), Parkinson's disease (PD), amyotrophic lateral sclerosis (ALS), multiple sclerosis (MS), Huntington disease (HD), HIV induced dementia and head trauma.

Finally, compounds of the invention can be used as a preventive treatment in those cases where a serious precancerous status has been highlighted or as support therapy along with conventional chemo-therapy for cancer treatment. Typical use of compounds of the invention is for prevention and treatment of colorectal cancer, breast, lung, bladder, prostate, cervix and skin cancer.

In another embodiment this invention provides methods for the preparation of compounds of Formula I.

In a further embodiment this invention provides pharmaceutical compositions for compounds of Formula I useful for the treatment of medical conditions wherein COX-2 over-activation underlies the pathologies above discussed. Within the scope of the present invention the term pharmaceutical composition (drug product) refers to any oral or parenteral dosage form suitable for the treatment of the above COX-2 mediated pathologies, that contains an effective amount of at least one of the active pharmaceutical ingredients (drug substances), compounds of formula (I) or solvates thereof, and a pharmaceutically acceptable carrier, excipients or diluents as defined below, for oral or parenteral administration.

DETAILED DESCRIPTION OF THE INVENTION

Considered the compounds included in the definitions of Formula I, it is clearly recognizable that the compounds of the invention can be divided in several sub-groups, one of them is the group wherein:

compounds of Formula I, in which Y is a carbonyl group (C=O), Z is hydroxy (—OH) or alkoxy (—OR$_3$), in this case compound of Formula I can be either acids or esters. Depending upon the meaning of X they can be either pyrrole-acetic acid derivatives, when X is hydrogen, or α-hydroxy and α-alkoxy acids or esters when X is respectively hydroxyl and alkoxy (—OR$_2$).

When X is hydrogen, compounds of Formula I wherein Z is hydroxy or a lower alkoxy group such as methoxy or ethoxy are not object of the present invention, whereas compounds of Formula I-a where Z is an higher alkoxy group: n-propyloxy, isopropyloxy, n-butyloxy, sec-butyloxy, iso-butyloxy are object of the present invention.

Formula I-a:

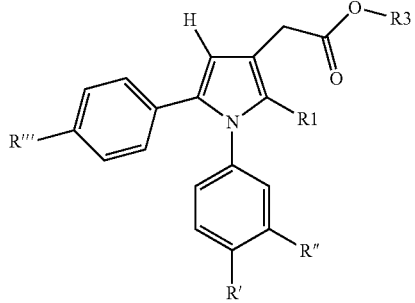

Compounds of Formula I wherein: Y is carbonyl
X is hydrogen
Z is hydroxyl or alkoxy
R$_3$ is an higher alkoxy group As before mentioned, some of these compounds demonstrated to be potent and selective in vitro inhibitors of COX-2 (J. Med. Chem., 2005, 48, 3428). More in detail: 2-[2-methyl-5-(4-methylsulphonyl)phenyl-1-phenyl-1H-pyrrol-3-yl]acetic acid (compound 1a), 2-[1-(4-methyl)phenyl-2-methyl-5-(4-methylsulphonyl)phenyl-1H-pyrrol-3-yl]acetic acid (compound 2a), 2-[1-(2-methyl-5-(4-methylsulphonyl)phenyl-4-(trifluoromethyl)phenyl-1H-pyrrol-3-yl]acetic acid (compound 3a), Ethyl 2-[2-methyl-5-(4-methylsulphonyl)phenyl-1-phenyl-1H-pyrrol-3-yl]acetate (compound 1b), Ethyl 2-[1-(4-methyl)phenyl-2-methyl-5-(4-methylsulphonyl)phenyl-1H-pyrrol-3-yl]acetate (compound 2b) and Ethyl 2-[2-methyl-5-(4-methylsulphonyl)phenyl-1-(4-trifluoromethyl)phenyl-1H-pyrrol-3-yl]acetate (Compound 3b) are in vitro potent and selective COX-2 inhibitors herein mentioned by reference.

In Table 1 in vitro COX inhibitory activity for these compounds is reported by reference.

TABLE 1

| Compound | COX-1 IC$_{50}$ (μM) | COX-2 IC$_{50}$ (μM) | COX-1/COX-2 Selectivity Index (IC$_{50}$ ratio) |
|---|---|---|---|
| 1a | >100 | 1.0 | >100 |
| 2a | >100 | 0.43 | >200 |
| 3a | >100 | 0.11 | >900 |
| 1b | >100 | 0.04 | >2500 |
| 2b | >100 | 0.48 | >200 |
| 3b | >100 | 0.06 | >1600 |

However, we surprisingly discovered that, though the previously reported compounds 1-3a and 1-3b are not endowed with any in vivo significant activity, compounds according to general Formula I, wherein Y is carbonyl (C=O), X is hydrogen, Z is an higher alkoxy group (n-propyloxy, iso-propyloxy, n-butyloxy, sec-butyloxy, iso-butyloxy) (Formula I-a) are unexpectedly very potent and effective also in several in vivo models, despite exhibiting similar COX-2 in vitro inhibitory potency.

Representative not limiting examples of compounds of Formula I-a are listed below:

Isopropyl [2-methyl-5-(4-methylsulphonyl)phenyl-1-phenyl-1H-pyrrol-3-yl]acetate (example 1).
Isopropyl [1-(3,4-difluoro)phenyl-2-methyl-5-(4-methylsulphonyl)phenyl-1H-pyrrol-3-yl]acetate (example 2). Isopropyl [1-(4-methoxy)phenyl-2-methyl-5-(4-methylsulphonyl)phenyl-1H-pyrrol-3-yl]acetate (example 3). Isopropyl [1-(3-fluoro)phenyl-2-methyl-5-(4-methylsulphonyl)phenyl-1H-pyrrol-3-yl]acetate (example 4). n-butyl [1-(3,4-difluoro)phenyl-2-methyl-5-(4-methylsulphonyl)phenyl-1H-pyrrol-3-yl]acetate (example 5). n-butyl [2-methyl-5-(4-methylsulphonyl)phenyl-1-phenyl-1H-pyrrol-3-yl]acetate (example 6).

In Table 2, COX in vitro inhibitory activities for representative compounds of Formula Ia are reported as an example and compared with known inhibitors.

TABLE 2

| Representative Compounds of Formula Ia | COX-1 IC$_{50}$ (μM) | COX-2 IC$_{50}$ (μM) | COX-1/COX-2 Selectivity Index (IC$_{50}$ ratio) |
|---|---|---|---|
| Example 1 | >100 | 0.0073 | >13600 |
| Example 2 | >100 | 0.021 | >4700 |
| Example 3 | >100 | 0.022 | >4500 |
| Example 4 | >100 | 0.043 | >2300 |
| Example 5 | >100 | 0.030 | >3300 |
| Example 6 | >100 | 0.014 | >7100 |

TABLE 2-continued

| Representative Compounds of Formula Ia | COX-1 IC$_{50}$ (µM) | COX-2 IC$_{50}$ (µM) | COX-1/COX-2 Selectivity Index (IC$_{50}$ ratio) |
|---|---|---|---|
| Celecoxib | 5.1 | 0.079 | 64.5 |
| Rofecoxib | >10 | 0.012 | >800 |

In Table 3, in vivo effects elicited by representative compounds of Formula I-a, disclosed in the present invention, in a rat model of hyperalgesia and edema induced by carragenine, are reported and compared with one representative lower alkyl ester within the groups of compounds 1-3a and 1-3b, along with a known COX-2 inhibitor. In Table 3 the in vivo efficacy for the most in vitro effective compound within the previously mentioned group of ethylesters (1-3a and 1-3b) along with further analogue ethylesters 4b and 5b, previously not disclosed (herein reported by reference), are reported for comparison with the compounds of the invention.

Compound 4b is: Ethyl 2-[1-(3-fluoro)phenyl-2-methyl-5-(4-methylsulphonyl)phenyl-1H-pyrrol-3-yl]acetate; its in vitro COX-2 inhibitory potency is IC$_{50}$=0.01 µM and the selectivity is >10000. Compound 5b is: Ethyl 2-[1-(3,4-difluoro)phenyl-2-methyl-5-(4-methylsulphonyl)phenyl-1H-pyrrol-3-yl]acetate; its in vitro COX-2 inhibitory potency is IC$_{50}$=0.02 µM and the selectivity is >5000.

TABLE 3

| Compound | Dosage | Analgesia 30 min MPE | Analgesia 60 min MPE | Edema inhibition 60 min; MPE |
|---|---|---|---|---|
| Example 1 | 5 mg/Kg | 80% | 60% | 100% |
| Example 2 | 20 mg/Kg | 100% | 70% | 91% |
| Example 3 | 20 mg/Kg | 67% | 90% | 77% |
| Example 4 | 20 mg/Kg | 84% | 80% | 87% |
| Example 5 | 20 mg/Kg | 76% | 100% | 74% |
| Compound 1b | 20 mg/Kg | 18% | 30% | 10% |
| Compound 4b | 20 mg/Kg | 28% | 40% | 30% |
| Compound 5b | 20 mg/Kg | 30% | 36% | 30% |
| Celecoxib | 20 mg/Kg | 73% | 81% | 95% |

MPE: Maximum percent effect.

In order to avoid any speculation that could ascribe the differences in vivo performance between the two groups of compounds to the used model, representative compounds of the two groups are compared in a rat model of hyperalgesia and edema induced by Zymosan.

In Table 4 Compound 5b and compound of the example 1 of this invention are compared in the rat Zymosan model. Also in this test compounds 1-3a and 1-3b did not highlight any significant in vivo activity.

TABLE 4

| Compound | Analgesia 0-2 hrs MPE | Analgesia 0-6 hrs MPE | Edema 0-2 hrs MPE | Edema 0-6 hrs MPE |
|---|---|---|---|---|
| Example 1 * | 75% | 70% | 20% | 15% |
| Compound 5b ** | 9% | 12% | 8% | 6% |
| Celecoxib *** | 30% | 35% | — | 24.8% |

* dose: 3 mg/Kg;
** dose: 4 mg/Kg;
*** dose: 3 mg/Kg.

In Table 5 in vivo effects elicited by compounds of Formula I-a in another animal model of analgesia (mouse writhing test) are reported.

TABLE 5

| Representative Compounds of Formula Ia | Number of mice | Dose s.c. mg/Kg | Number of writhes |
|---|---|---|---|
| Control | 18 | — | 38.1 ± 2.6 |
| Example 1 | 8 | 5 | 28.5 ± 3.3 |
| Example 2 | 12 | 20 | 21.5 ± 3.9 |
| Example 3 | 12 | 20 | 18.5 ± 3.5 |
| Example 4 | 9 | 20 | 17.7 ± 2.9 |
| Example 5 | 30 | 20 | 13.7 ± 4.0 |

Effects of compounds of the invention in the mouse abdominal constriction test (acetic acid 0.6%).

All drugs were administered 30 min before test. Vehicle: DMSO: H$_2$O 1:3

Another group of compounds of Formula I is the group wherein Y is a carbonyl group (C=O), Z is hydroxy (—OH) or alkoxy (—OR$_2$), and X is independently selected from hydroxyl (—OH) and alkoxy (—OR$_2$), in this case compounds of Formula I can be α-hydroxy and α-alkoxy acids or esters of Formula I-b, where R1, R', R" and R'" are as defined for compounds of Formula I.

Compounds of Formula I-b:

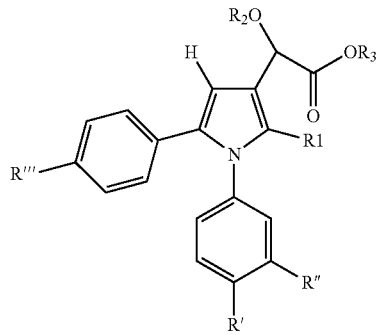

Compounds of Formula I wherein: Y is carboxy
Z is hydroxy or alkoxy
X is hydroxy or alkoxy In compounds of Formula I-b the R$_2$ and R$_3$ groups can be independently selected from the meanings above detailed for compounds of formula I. Accordingly, compounds of Formula I-b can be α-hydroxy esters or α-alkoxy acids as well as, for instance, α-methoxy-isopropylesters or α-ethoxy-methylesters, by independently attributing the several meaning of R$_2$ and R$_3$ reported for compounds of Formula I.

Representative not limiting examples of compounds of Formula I-b are listed below:

Ethyl[2-hydroxy-2-[2-methyl-5-(4-methylsulphonyl)phenyl-1-phenyl-1H-pyrrol-3-yl]]acetate (example 7). Ethyl [2-hydroxy-2-[1-(4-methoxy)phenyl-2-methyl-5-(4-methylsulphonyl)phenyl-1H-pyrrol-3-yl]]acetate (example 8). Ethyl[2-hydroxy-2-[1-(3-fluoro)phenyl-2-methyl-5-(4-methylsulphonyl)phenyl-1H-pyrrol-3-yl]]acetate (example 9). Ethyl[2-ethoxy-2-[-2-methyl-5-(4-methylsulphonyl)phenyl-1-phenyl-1H-pyrrol-3-yl]]acetate (example 10). Ethyl[2-ethoxy-2-[1-(4-methoxy)phenyl-2-methyl-5-(4-methylsulphonyl)phenyl-1H-pyrrol-3-yl]]acetate (example 11). Ethyl[2-ethoxy-2-[1-(3-fluoro)phenyl-2-methyl-5-(4-methylsulphonyl)phenyl-1H-pyrrol-3-yl]]acetate (example 12).

In Table 6, COX in vitro inhibitory activities for representative compounds of Formula I-b are reported as an example.

TABLE 6

| Representative compounds of Formula Ib | COX-1 IC$_{50}$ (μM) | COX-2 IC$_{50}$ (μM) | COX-1/COX-2 Selectivity Index (IC$_{50}$ ratio) |
| --- | --- | --- | --- |
| Example 7 Racemic mixture | >100 | 0.30 | >333 |
| Example 7a (+) enantiomer | >100 | 0.18 | >550 |
| Example 7b (−) enantiomer | >100 | 0.15 | >650 |
| Example 8 Racemic mixture | >100 | 0.12 | >830 |
| Example 8a (+) enantiomer | >100 | 0.079 | >1200 |
| Example 8b (−) enantiomer | >100 | 0.15 | >650 |
| Example 9 Racemic mixture | >100 | 0.32 | >310 |
| Example 9a (+) enantiomer | >100 | 1.1 | >1300 |
| Example 9b (−) enantiomer | >100 | 0.075 | >650 |

In Table 7, in vivo effects exerted by a representative compound of Formula I-b, on hyperalgesia and edema induced by carragenine, in a rat model, is reported as an example.

TABLE 7

| Representative compound of Formula Ib | Dose | Analgesia 30 min MPE | Analgesia 60 min MPE | Edema inhibition 60 min; MPE |
| --- | --- | --- | --- | --- |
| Example 9 | 20 mg/Kg | 80% | 40% | 40% |

Another group of compounds of Formula I is the group wherein Y is a carbonyl group (C=O), Z is amino (—NH$_2$), alkylamino or arylamino (—NHR$_3$), dialkylamino or alkylarylamino (NR$_2$R$_3$), X is independently selected from hydrogen, hydroxyl (—OH), alkoxy (—OR$_2$), wherein the R$_3$ and R$_2$ groups can be independently selected from the meanings listed for compounds of Formula I. In this case compounds of Formula I become amides of Formula I-c, wherein R', R" and R'" are as generally defined for compounds of Formula I.

Compounds of Formula I-c:

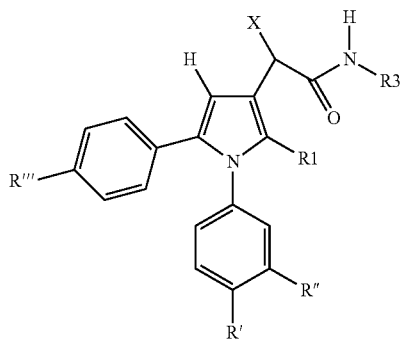

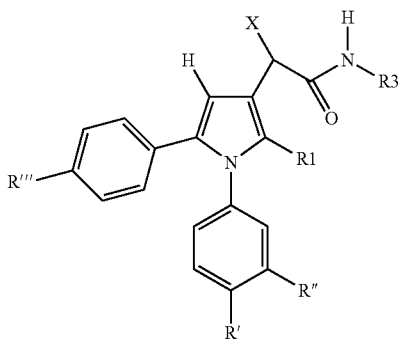

Compounds of Formula I wherein: Y is Carbonyl
Z is amino, alkylamino, arylamino, alkylarylamino
X is hydrogen, hydroxy or alkoxy Representative not limiting examples of compounds of formula Ic are listed below:

N-methyl [1-phenyl-2-methyl-5-(4-methylsulphonyl)phenyl-1H-pyrrol-3-yl]acetamide (example 13). N-Ethyl-[2-methyl-5-(4-methylsulphonyl)phenyl-1-phenyl-1H-pyrrol-3-yl]acetamide (example 14). N,N-Dimethyl-[2-methyl-5-(4-methylsulphonyl)phenyl-1-phenyl-1H-pyrrol-3-yl]acetamide (example 15). N-methyl-N-benzyl [1-(4-fluoro)phenyl-2-methyl-5-(4-methylsulphonyl)phenyl-1H-pyrrol-3-yl]acetamide (example 16). N-Methyl-[2-methyl-5-(4-methylsulphonyl)phenyl-1-(4-trifluoromethyl)phenyl-1H-pyrrol-3-yl]acetamide (example 17). N-ethyl [1-(4-trifluoromethyl)phenyl-2-methyl-5-(4-methylsulphonyl)phenyl-1H-pyrrol-3-yl]acetamide (example 18). N-methyl-N-benzyl [1-(4-trifluoromethyl)phenyl-2-methyl-5-(4-methylsulphonyl)phenyl-1H-pyrrol-3-yl]acetamide (example 19).

In Table 8, COX in vitro inhibitory activities for representative compounds of Formula I-c are reported as an example.

TABLE 8

| Representative compounds of Formula I-c | COX-1 IC$_{50}$ (μM) | COX-2 IC$_{50}$ (μM) |
| --- | --- | --- |
| Example 13 | >100 | 1.00 |
| Example 14 | >100 | 0.35 |
| Example 15 | >100 | 0.58 |
| Example 16 | >100 | 0.17 |
| Example 17 | >100 | 0.09 |
| Example 18 | >100 | 0.19 |
| Example 19 | >100 | 0.47 |

Another group of compounds of Formula I is the group wherein Y is a methylene group (—CH$_2$—), Z is independently selected from hydroxy (—OH) and alkoxy (—OR$_3$) groups, X is independently selected from hydrogen, hydroxyl (—OH), alkoxy (—OR$_2$), being the R$_2$ and R$_3$ groups independently selected from the meanings listed for compounds of Formula I. In this case compound of Formula I are alcohols and ethers of Formula I-d, wherein R', R" and R'" are as defined for compounds of Formula I.

Compounds of formula I-d:

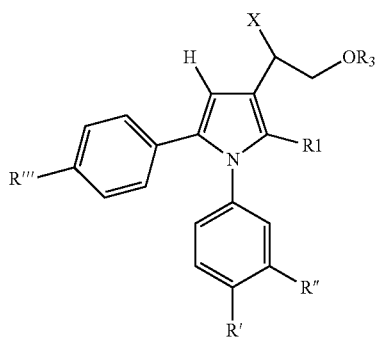

Compound of Formula I wherein: Y is methylene
Z is hydroxy or alkoxy
X is hydrogen, hydroxy or alkoxy Representative not limiting examples of compounds of Formula I-d are listed below:

[2-Methyl-5-(4-methylsulphonyl)phenyl-3-(2-methoxyethyl)-1-phenyl]-1H-pyrrole (example 20). [3-(2-Ethoxyethyl)-2-methyl-5-(4-methylsulphonyl)phenyl-1-phenyl]-1H-pyrrole (example 21). [2-Methyl-5-(4-methylsulphonyl)phenyl-1-phenyl-3-(2-n-propyloxyethyl)]-1H-pyrrole (example 22). [1-(4-Fluoro)phenyl-2-methyl-5-(4-methylsulphonyl)phenyl-3-(2-methoxyethyl)]-1H-pyrrole (example 23). [3-(2-Ethoxyethyl)-1-(4-Fluoro)phenyl-2-methyl-5-(4-methylsulphonyl)phenyl]-1H-pyrrole (example 24). [1-(4-Fluoro)phenyl-2-methyl-5-(4-methylsulphonyl)phenyl-3-(2-n-propyloxyethyl)]-1H-pyrrole (example 25). [2-Methyl-5-(4-methylsulphonyl)phenyl-3-(2-methoxyethyl)-1-(4-trifluoromethyl)phenyl]-1H-pyrrole (example 26). [3-(2-Ethoxyethyl)-2-methyl-5-(4-methylsulphonyl)phenyl-1-(4-trifluoromethyl)phenyl]-1H-pyrrole (example 27). [2-Methyl-5-(4-methylsulphonyl)phenyl-3-(2-n-propyloxyethyl)-1-(4-trifluoromethyl)phenyl]-1H-pyrrole (example 28).

In Table 9, COX in vitro inhibitory activities for representative compounds of Formula I-d are reported as an example.

TABLE 9

| Representative compounds of Formula I-d | COX-1 IC$_{50}$ (μM) | COX-2 IC$_{50}$ (μM) |
| --- | --- | --- |
| Example 20 | >100 | 0.048 |
| Example 21 | >100 | 0.015 |
| Example 22 | >100 | 0.018 |
| Example 23 | >100 | 0.018 |
| Example 24 | >100 | 0.047 |
| Example 25 | >100 | 0.030 |
| Example 26 | >100 | 0.049 |
| Example 27 | >100 | 0.085 |
| Example 28 | >100 | 0.11 |

In Table 10, in vivo effects exerted by representative compounds of Formula I-d, on hyperalgesia and edema induced by carragenine, in a rat model, are reported as an example.

TABLE 10

| Representative compounds of Formula I-d | Dose | Analgesia 30 min MPE | Analgesia 60 min MPE | Edema inhibition 60 min; MPE |
| --- | --- | --- | --- | --- |
| Example 21 | 20 mg/Kg | 96% | 72% | 45% |
| Example 22 | 20 mg/Kg | 88% | 94% | 43% |
| Example 25 | 20 mg/Kg | 53% | 70% | 41% |

Another group of compounds of Formula I is the group wherein Y is a methylene group (—CH$_2$—), Z is an alkylcarboxyl or arylcarboxyl (—OCOR$_3$) group, X is independently selected from hydrogen, hydroxyl (—OH), alkoxy (—OR$_2$), the R$_2$ and R$_3$ groups being independently selected from the meanings listed for compounds of Formula I. In this case compounds of Formula I are esters of Formula I-e, wherein R', R" and R''' are as generally defined for compounds of Formula I.

Compounds of formula I-e:

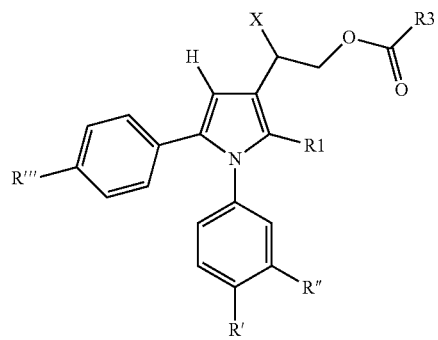

Compound of Formula I wherein: Y is methylene
Z is alkylcarboxyl or arylcarboxyl
X is hydrogen, hydroxy or alkoxy Representative not limiting examples of compounds of Formula I-e are listed below:

2-[1-(4-Fluorophenyl)-2-methyl-5-(4-methylsulphonyl)phenyl-1H-pyrrol-3-yl]ethyl propionate (example 29). 2-[1-(4-fluorophenyl)-2-methyl-5-(4-methylsulphonyl)phenyl-1H-pyrrol-3-yl]ethyl butanoate (example 30). 2-[1-(4-fluorophenyl)-2-methyl-5-(4-methylsulphonyl)phenyl-1H-pyrrol-3-yl]ethyl benzoate (example 31). 2-[1-(4-fluorophenyl)-2-methyl-5-(4-methylsulphonyl)phenyl-1H-pyrrol-3-yl]ethyl-2-fluorobenzoate (example 32). 2-[1-(4-fluorophenyl)-2-methyl-5-(4-methylsulphonyl)phenyl-1H-pyrrol-3-yl]ethyl-4-fluorobenzoate (example 33). 2-[1-(4-fluorophenyl)-2-methyl-5-(4-methylsulphonyl)phenyl-1H-pyrrol-3-yl]ethyl 2-tiophencarboxylate (example 34). 2-[1-(4-fluoro)phenyl-2-methyl-5-(4-methylsulphonyl)phenyl-1H-pyrrol-3-yl]ethyl isopropionate. 2-[1-(4-fluoro)phenyl-2-methyl-5-(4-methylsulphonyl)phenyl-1H-pyrrol-3-yl]ethyl isobutyrate.

In Table 11, COX in vitro inhibitory activities for representative compounds of Formula I-e are reported as an example.

TABLE 11

| Representative compounds of Formula I-e | COX-1 IC$_{50}$ (μM) | COX-2 % of inhibition at $1.10^{-5}$ M |
|---|---|---|
| Example 29 | >100 | 97% |
| Example 30 | >100 | 86% |
| Example 31 | >100 | 76% |
| Example 32 | >100 | 64% |
| Example 33 | >100 | 69% |
| Example 34 | >100 | 69% |

Another group of compounds of Formula I is the one wherein Y is a methylene group (—CH$_2$—), Z is an amide (—NH—CO—R$_3$), X is independently selected from hydrogen, hydroxyl (—OH), alkoxy (—OR$_2$), being the R$_3$ groups independently selected from the meanings listed for compounds of Formula I; in this case compounds of Formula I are amides of Formula I-f, wherein R', R" and R'" are as defined for compounds of Formula I.

Compounds of formula I-f:

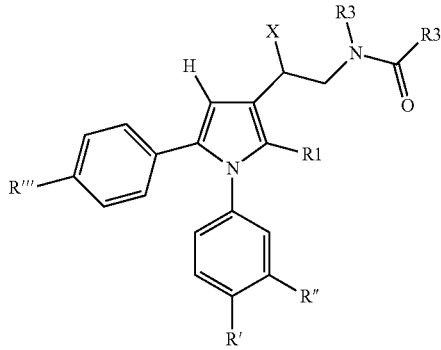

Compound of Formula I wherein: Y is methylene
Z is aminocarbonlyl alkyl or aminocarbonlyl aryl
X is hydrogen, hydroxy or alkoxy Representative not limiting examples of compounds of Formula I-f are listed below:
N-[2-[1-(4-Fluorophenyl)-2-methyl-5-(4-(methylsulphonyl)phenyl)-1H-pyrrol-3-yl]ethyl]benzamide (example 35). N-[2-[1-(4-fluoro)phenyl-2-methyl-5-(4-methylsulphonyl)phenyl-1H-pyrrol-3-yl]ethyl]propanamide. N-[2-[1-(4-fluoro)phenyl-2-methyl-5-(4-methylsulphonyl)phenyl-1H-pyrrol-3-yl]ethyl]butanamide. N-[2-[1-(4-fluoro)phenyl-2-methyl-5-(4-methylsulphonyl)phenyl-1H-pyrrol-3-yl]ethyl 2-fluorobenzamide. N-[2-[1-(4-fluoro)phenyl-2-methyl-5-(4-methylsulphonyl)phenyl-1H-pyrrol-3-yl]ethyl 4-fluorobenzamide. N-[2-[1-(4-fluoro)phenyl-2-methyl-5-(4-methylsulphonyl)phenyl-1H-pyrrol-3-yl]ethyl 2-thienoamide.

Another group of compounds of Formula I is the group wherein Y is a methylene group (—CH$_2$—), Z is independently selected from the carbamate groups (—O—CO—NHR$_3$) or the carbonates (—O—CO—OR$_3$), X is independently selected from hydrogen, hydroxyl (—OH), alkoxy (—OR$_2$), the R$_2$ and R$_3$ groups being independently selected from the meanings listed for compounds of Formula I; in this case compounds of Formula I are carbamates or carbonates of Formula I-g, wherein R', R" and R'" are as defined for compounds of Formula I.

Compounds of formula I-g:

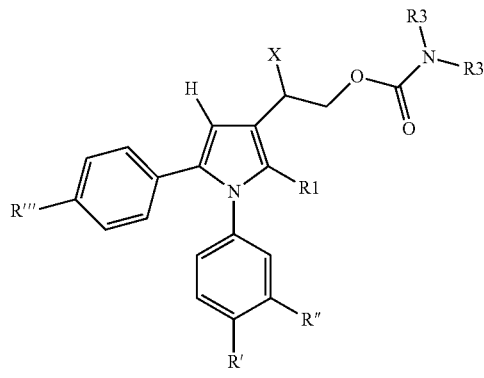

Carbamate of formula I-g

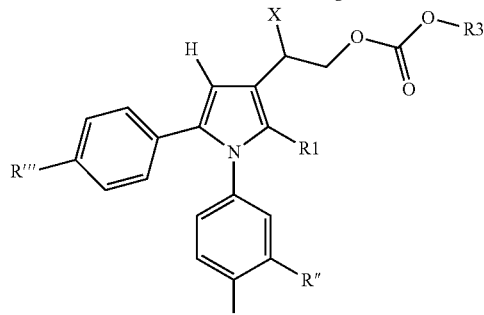

Carbamate of formula I-g

Compound of Formula I wherein: Y is methylene
Z is an alkyl or aryl carbamate or carbonate
X is hydrogen, hydroxy or alkoxy Representative not limiting examples of compounds of Formula I-g are listed below:
N-propyl-2-[2-Methyl-5-[4-(methylsulphonyl)phenyl]-1-phenyl-1H-pyrrol-3-yl]ethyl]carbamate (example 36). N-Ethyl-[2-[1-(4-fluoro)phenyl-2-methyl-5-(4-methylsulphonyl)phenyl-1H-pyrrol-3-yl]ethyl carbamate. N-propyl-[2-[1-(4-fluoro)phenyl-2-methyl-5-(4-methylsulphonyl)phenyl-1H-pyrrol-3-yl]ethyl]-carbamate. N-Phenyl-[2-[1-(4-fluoro)phenyl-2-methyl-5-(4-methylsulphonyl)phenyl-1H-pyrrol-3-yl]ethyl]carbamate. Methyl-[2-[1-phenyl-2-methyl-5-(4-methylsulphonyl)phenyl-1H-pyrrol-3-yl]ethyl]carbonate (example 37). Ethyl-[2-[1-phenyl-2-methyl-5-(4-methylsulphonyl)phenyl-1H-pyrrol-3-yl]ethyl]carbonate. Propyl-[2-[1-phenyl-2-methyl-5-(4-methylsulphonyl)phenyl-1H-pyrrol-3-yl]ethyl]carbonate. Phenyl-[2-[1-phenyl-2-methyl-5-(4-methylsulphonyl)phenyl-1H-pyrrol-3-yl]ethyl]carbonate. Methyl-[2-[1-(4-fluoro)phenyl-2-methyl-5-(4-methylsulphonyl)phenyl-1H-pyrrol-3-yl]ethyl]carbonate. Ethyl-[2-[1-(4-fluoro)phenyl-2-methyl-5-(4-methylsulphonyl)phenyl-1H-pyrrol-3-yl]ethyl]carbonate. Propyl-[2-[1-(4-fluoro)phenyl-2-methyl-5-(4-methylsulphonyl)phenyl-1H-pyrrol-3-yl]ethyl]carbonate. Phenyl-[2-[1-(4-fluoro)phenyl-2-methyl-5-(4-methylsulphonyl)phenyl-1H-pyrrol-3-yl]ethyl]carbonate.

The last group of compounds of Formula I is the one wherein Y is a methylene group (—CH$_2$—), Z is independently selected from the carbamate group (—NH—CO—OR$_3$) or the urea group (—NH—CO—NHR$_3$), X is independently selected from hydrogen, hydroxyl (—OH), alkoxy (—OR$_2$), being the R$_2$ and R$_3$ groups independently selected from the meanings listed for compounds of Formula I; in this case compounds of Formula I are carbamates or ureas of Formula I-h, wherein R', R" and R'" are as defined for compounds of Formula I.

Compounds of Formula I-h:

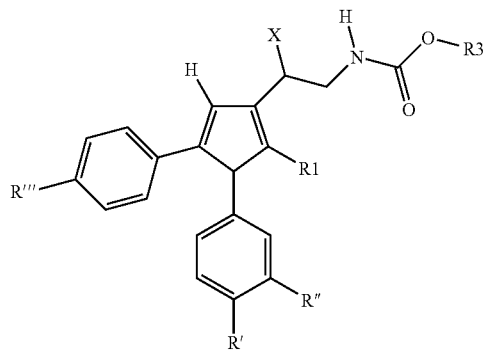

Carbamates of Formula I-h

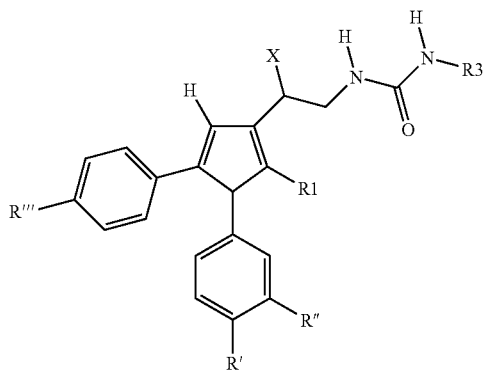

Ureas of Formula I-h

Compounds of Formula I wherein: Y is methylene
Z is alkylor or aryl aminocarbomoyl or urea
X is hydrogen, hydroxy or alkoxy Representative not limiting examples of compounds of formula I-h are listed below:

Propyl-N-[2-[2-methyl-5-(4-methylsulphonyl)phenyl-1-phenyl-1H-pyrrol-3-yl]ethyl]carbamate (example 38). Methyl-N-[2-[2-methyl-5-(4-methylsulphonyl)phenyl-1-phenyl-1H-pyrrol-3-yl]ethyl]carbamate. Ethyl-N-2-[2-methyl-5-(4-methylsulphonyl)phenyl-1-phenyl-1H-pyrrol-3-yl]ethyl]carbamate. Methyl-N-[2-[2-methyl-5-(4-methylsulphonyl)phenyl-1-(4-fluoro-phenyl)-1H-pyrrol-3-yl]ethyl]carbamate. Ethyl-N-[2-[2-methyl-5-(4-methylsulphonyl)phenyl-1-(4-fluorophenyl)-1H-pyrrol-3-yl]ethyl]carbamate. Propyl-N-[2-[2-methyl-5-(4-methylsulphonyl)phenyl-1-(4-fluorophenyl)-1H-pyrrol-3-yl]ethyl]carbamate. Propyl N-[2-[2-methyl-5-(4-methylsulphonyl)phenyl-1-phenyl-1H-pyrrol-3-yl]ethyl] urea (Example 39). Methyl N-[2-[2-methyl-5-(4-methylsulphonyl)phenyl-1-phenyl-1H-pyrrol-3-yl]ethyl] urea. Ethyl N-[2-[2-methyl-5-(4-methylsulphonyl)phenyl-1-phenyl-1H-pyrrol-3-yl]ethyl]urea. Methyl N-[2-[2-methyl-5-(4-methylsulphonyl)phenyl-1-(4-fluorophenyl)-1H-pyrrol-3-yl]ethyl]urea. Ethyl N-[2-[2-methyl-5-(4-methylsulphonyl)phenyl-1-(4-fluorophenyl)-1H-pyrrol-3-yl]ethyl]urea. Propyl N-[2-[2-methyl-5-(4-methylsulphonyl)phenyl-1-(4-fluorophenyl)-1H-pyrrol-3-yl]ethyl]urea.

Synthesis of Compounds of the Invention

The general process for the preparation of representative examples of compounds of Formula I is described in Scheme 1.

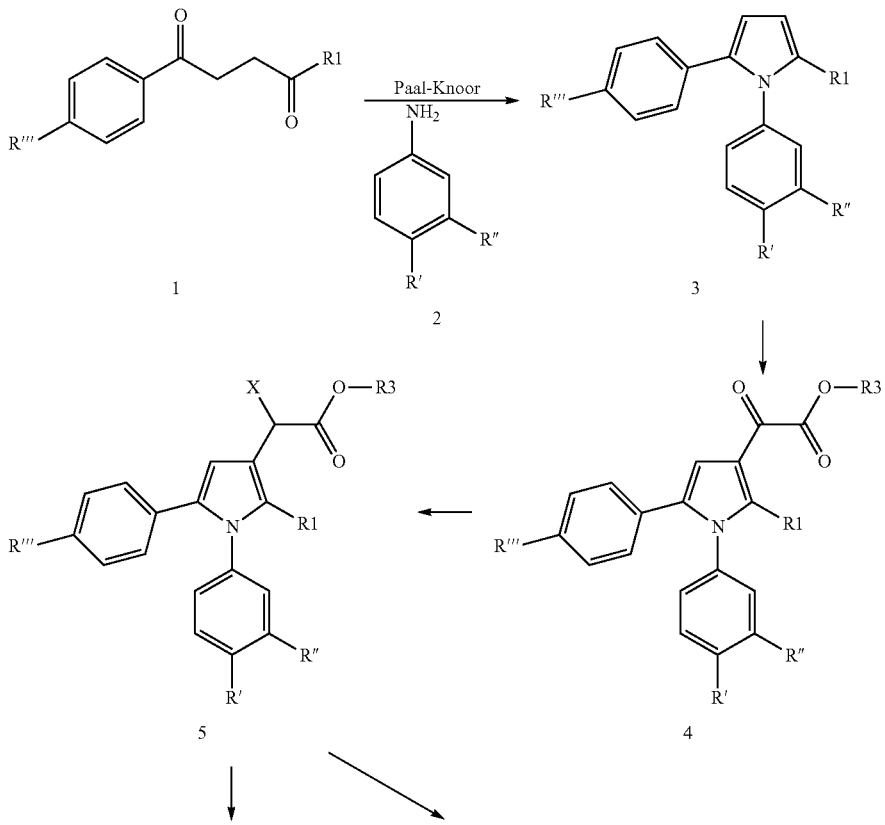

Scheme 1

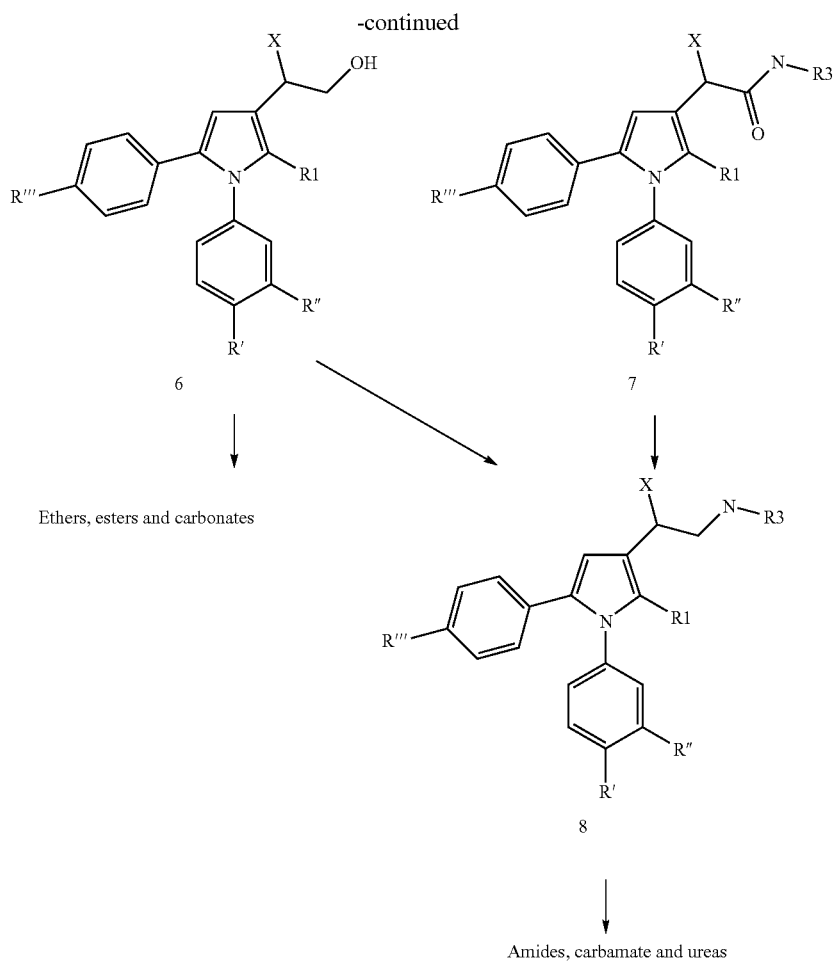

Ethers, esters and carbonates

Amides, carbamate and ureas

The synthesis of the compounds of the invention involves the preparation of suitably substituted 1,5-diaryl-2-alkyl pyrroles according to Paal-Knoor condensation, consisting of thermal cyclization of an appropriately substituted 1,4-diketone (1; Scheme 1) with the aniline (2). The functionalization of position 3, involves a regioselective acylation of the pyrrole 3 with ethoxoxalyl chloride to give the ketoester 4, which is in turn converted into pyrrolacetic derivatives 5. Pyrrole derivatives 5 can be directly converted into compounds of Formula I-a, reduced to alcohols 6, or converted into amides 7 (compounds of Formula I-b), which can be consecutively reduced to amines 8, intermediates for obtaining carbamates and ureas of Formula I-h. Alternatively, amine 8 can be prepared starting from alcohols 6. By treatment with phosphorous tribromide in chloroform at room temperature the alcohols were converted into the respective bromoethyl derivatives which, via the classic Gabriel synthesis, were transformed into 2-aminoethyl derivatives. These compounds were, in turn, acylated by the suitable acyl chloride to afford the carboxamido derivatives of formula I-f. Alcohols 6 can be converted into ethers (compound of Formula I-d), esters (compounds of Formula I-e) or carbamate and carbonates (compounds of Formula I-g) as depicted in Scheme 1. Appropriately substituted starting 1,4-diketones (1) are obtained by condensing a suitably substituted benzaldehyde with methyl vinyl ketone according to Stetter conditions.

Reduction of the ketoester 4 into derivatives 5 can be achieved when X is —OH, using reducing agents such as sodium-borohydride in the presence of tertbutanol; compounds of Formula I where is X=H can be obtained by reducing derivatives 4 with triethylsilane and trifluoroacetic acid (J. Med. Chem., 2005, 48, 3428). Compounds of Formula I where X is —OR$_2$ can be obtained by reduction of the ketoester 4 using reducing agents such as sodiumborohydride in the presence of the appropriate alcohol (—OR$_2$). Alternatively, compounds of Formula I where X is —OR$_2$ can be obtained by conversion of compounds 5 where X is —OH into compounds 5 where X is —OR$_2$ by conventional ether synthesis. Which consists in treating the alcohols 5 with the appropriate alkyl bromide or iodide (R$_2$—Br or R$_2$—I) in the presence of a base, such us potassium carbonate, in a suitable solvent such as for example dimethylformamide or toluene and optionally with the addition of a phase transfer catalyst. Alternatively, the alcohol 5 can be converted into its sodium or lithium salt by treatment with a suitable base, such as sodium hydride, sodium ethoxyde, lithium hydride or t-butyl lithium in an appropriate solvent such as dimethylformamide, ethanol or tetrahydrofurane, and then reacting the obtained alkoxyde with the appropriate alkyl bromide. Another approach to obtain compounds where X is —OR$_2$ from intermediates where X is —OH, is conversion of the hydroxyl into a triflate or a tosilate or an halide (Br, I), according to standard methods, and the reacting it with a proper alkoxide (M—OR$_2$), where M is an alkaline metal. The compounds of Formula I-a can be obtained by reacting compounds 3 with oxalyl chloride and then quenching the obtained acyl chloride into the appropriate alcohol (—OR₃). Alternatively, the compounds of Formula I-a can be obtained from esters 5, where R₃ is methyl or ethyl by reaction with an appropriate amount of sodium or lithium or potassium alkoxyde (M—OR₃), such as sodium isopropoxide, sodium n-propoxide, sodium sec-butoxide or sodium t-butoxide as well as the corresponding lithium or potassium salts, in a suitable solvent such as isopropanol, sec-butanol, t-butanol, toluene, tetrahydrofurane or dimethylformamide. Alternatively, esters 5 can be hydrolyzed to the corresponding acids, and then converted into compounds of Formula I-a by activation for example by mixed anhydrides, carbonyldiimidazole or carbodiimides (DDC, WSC) and reacting the reactive intermediate with the appropriate alcohol. In this last case, when X is OH, protection is necessary before carboxylate activation, suitable hydroxyl protecting group are silyl ethers such as dimethyl-tert-butyl silyl ethers, allyl ether or benzyl ethers.

Reduction of amides 7 into amines 8, is an alternative approach to the Gabriel synthesis mentioned above. This reduction can be achieved by usual reducing agents such as lithium-alluminium hydride, borane in tetrahydrofurane. Amines 8 can be converted into carbamates and ureas of formula I-h by standard procedures, for example by reacting carbonyl diimidazole with the appropriate alcohol and then with the amine 8 to obtain the carbamate, or reacting the amine 8 with carbonyl diimidazole and subsequently with the appropriate amine to obtain the ureas. Alternatively, amines 8 can be reacted with suitable chloroformates such as isobutyl chloroformate, isopropyl chloroformate, ethyl or methylchloroformate in the presence of an organic base such as diisopropylethilamine, triethylamine or any other suitable organic base and in an organic solvent, alternatively Schotten-Bauman conditions can be used to provide carbamates of formula I-h.

Amines of formula 8 can alternatively obtained from alcohols of formula 6, by oxidation to aldehyde followed by reductive amination using the appropriate amine. Oxidation of alcohols 6 can be obtained by usual procedures such as PCC or PDC oxidation, or Swern's oxidation. For those cases where in the alcohol of formula 6 X is —OH, this hydroxyl must be protected as above discussed, before reduction of the ester 5, suitable protecting groups are dimethyl-tertbutylsilyl, benzyl and trityl. Reductive amination of the intermediate aldheyde can be obtained by standard procedures such as reaction with the amine in a suitable solvent such as toluene to obtain the imine which is subsequently reduced to the amine by reaction with sodium borohydride, sodium cyanoborohydride or catalytic hydrogenation. Alternatively, the amine 8 can be directly obtained by reductive amination of the intermediate aldehyde by its direct reaction with the appropriate amine, in the presence of a reducing agent such as sodium cyanoborohydride, in methanol or ethanol or tetrahydrofurane. Esters of Formula I-e can be obtained from alcohols 6 by reaction with the appropriate acylchloride or mixed anhydride in the presence of a base according to standard methods. Alternatively, alcohols 6 can be reacted with the appropriate carboxylic acid in the presence of a condensing agent such as DCC, WSC or carbonyl diimidazole, of an organic base and in a suitable organic solvent. For those alcohol of formula 6 where X is —OH, in some cases expecially when acylchlorides or mixed anhydrides are used, this hydroxyl must be protected as above discussed. Carbamates of Formula I-g can be obtained from alcohols 6 by reaction with carbonyl diimidazole followed by the appropriate amine in a suitable solvent such as dichloromethane, tetrahydrofurane or dimethylformamide. Analogously carbonates of Formula I-g can be obtained from alcohols 6 by reaction with carbonyl diimidazole followed by the appropriate alcohol, in a suitable solvent such as dichloromethane, tetrahydrofurane or dimethylformamide. Alternatively, the carbonyldiimidazole adduct of the alcohol 6 can be treated with the appropriate lithium, sodium or potassium alkoxyde in a solvent such as dimethylformamide or toluene. Alternatively, carbonates of Formula I-g can be obtained from alcohols 6 by reaction with phosgene or tri-phosgene followed by the appropriate alcohol. For some compounds of Formula I it should be necessary the introduction of the sulphonyl group at the last step or at a penultimate step of the synthesis. In these cases the sulphonyl group either in R' or R''' position can be obtained by oxidation of the corresponding methyl-thioether using meta-chloroperbenzoic acid or oxone.

The following examples are depicted to better illustrate the invention:

EXAMPLES

Example 1

Isopropyl[2-methyl-5-(4-methylsulphonyl)phenyl-1-phenyl-1H-pyrrol-3-yl]acetate

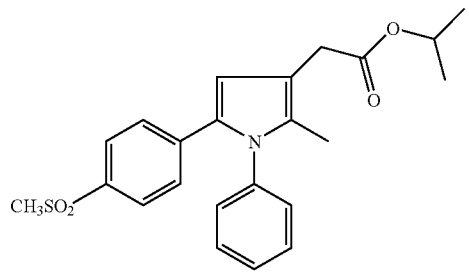

To a solution of isopropyl-2-methyl-5-[4-methylsulphonyl)phenyl]-1-phenyl-1H-pyrrole-3-glyoxylate (2.3 mmol) in trifluoroacetic acid (TFA) (9 mL) stirred at 0° C. under nitrogen, triethylsilane (0.75 mL, 4.7 mmol) was slowly added and the mixture was stirred for 30 min at room temperature. At the end of the reaction the mixture was made alkaline with 40% aqueous ammonia and extracted with CHCl₃. The organic solution was dried and evaporated in vacuo. The resulting residue was chromatographed on silica gel eluting with CHCl₃ to give a solid which after re-crystallization from hexane/ethyl acetate afforded the required product. Yellowish needles (yield 55%); Mp 112° C. NMR (CDCl₃) 7.67-7.69 (d, 2H), 7.43-7.44 (m, 3H), 7.16-7.18 (d, 2H), 7.11-7.13 (m, 2H), 6.50 (s, 1H), 5.30-5.35 (m, 1H), 3.45 (s, 2H), 2.96-2.98 (s, 3H), 2.04 (s, 3H) 1.24-1.25 (d, 6H). Anal. (C₂₃H₂₅NO₄S) C, H, N, O, S.

Isopropyl-2-methyl-5-[4-methylsulphonyl)phenyl]-1-phenyl-1H-pyrrole-3-glyoxylate

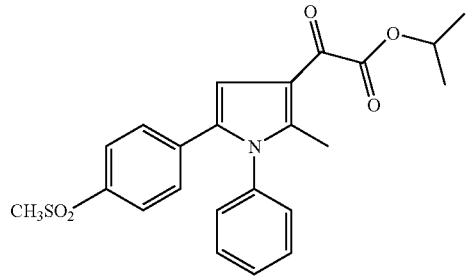

A solution of 2,6-lutidine (10 mmol) and oxalyl chloride (0.76 mL, 10 mmol) was added to a stirred solution of 2-Methyl-5-[4-(methylsulphonyl)phenyl]-1-phenyl-1H-pyrrole (10 mmol), in anhydrous dichloromethane (15 mL) and under nitrogen atmosphere. The solution was stirred for 4 h at 0° C. Immediately after, the isopropyl alcohol (20 mmol) was added dropwise. The solution was stirred for 30 min at room temperature. At the end the mixture was poured on ice and extracted with dichloromethane. The organic solution was dried and evaporated in vacuo. Purification of the residue by flash chromatography with ethyl acetate as eluent gave a solid which after re-crystallization from hexane/ethyl acetate afforded the expected product. Yellowish needles (yield 76%); Mp 160° C. NMR (CDCl$_3$) 7.67-7.69 (d, 2H), 7.43-7.44 (m, 3H), 7.16-7.18 (d, 2H), 7.11-7.13 (m, 2H), 7.04-7.05 (s, 1H), 5.30-5.35 (m, 1H), 2.97-2.98 (s, 3H), 2.43-2.44 (s, 3H) 1.38-1.40 (d, 6H). Anal. (C$_{23}$H$_{23}$NO$_5$S) C, H, N, O, S.

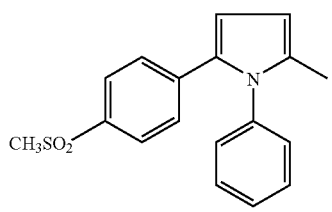

2-Methyl-5-[4-(methylsulphonyl)phenyl]-1-phenyl-1H-pyrrole (3a) prepared in 80% yield as reported in the literature (Biava et al., J. Med. Chem., 2005, 48, 3428).

Example 2

Isopropyl[1-(3,4-difluoro)phenyl-2-methyl-5-(4-methylsulphonyl)phenyl-1H-pyrrol-3-yl]acetate

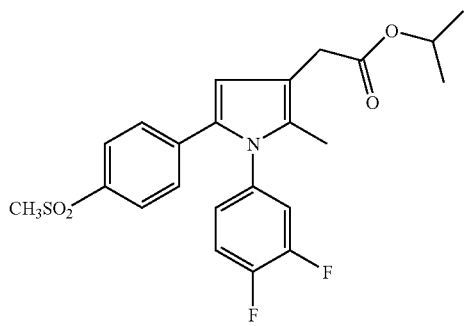

Prepared according to the procedure described in example 1, in 45% yield starting from isopropyl-2-methyl-5-[4-methylsulphonyl)phenyl]-1-(3,4-difluorophenyl)-1H-pyrrole-3-glyoxylate; Yellowish needles Mp 143° C.; NMR (CDCl$_3$) 7.69-7.71 (m, 2H), 7.16-7.19 (m, 3H), 6.92-7.10 (m, 2H), 6.50-6.61 (s, 1H), 5.26 (m, 1H), 3.45-3.47 (s, 2H), 3.01-3.03 (s, 2H), 2.07-2.09 (s, 3H), 1.23-1.30 (t, 6H). Anal. (C$_{23}$H$_{23}$F$_2$NO$_4$S) C, H, N, F, O, S.

Isopropyl-2-methyl-5-[4-methylsulphonyl)phenyl]-1-(3,4-difluorophenyl)-1H-pyrrole-3-glyoxylate

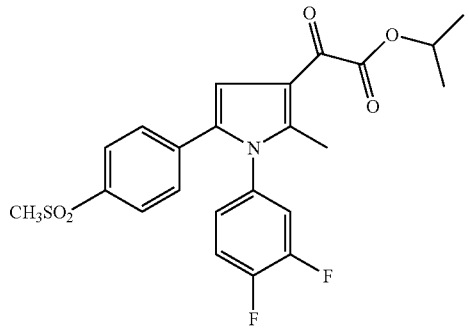

Prepared according to the procedure described in example 1, in 65% yield starting from 2-methyl-5-[4-methylsulphonyl)phenyl]-1-(3,4-difluorophenyl)-1H-pyrrole; yellowish needles; Mp 60° C.; NMR (CDCl$_3$) 7.74-7.78 (m, 2H), 7.23-7.26 (m, 3H), 7.04-7.05 (m, 3H), 5.26 (m, 1H), 2.94-3.00 (s, 3H), 2.42-2.46 (s, 3H), 1.33-1.41 (d, 6H). Anal. (C$_{23}$H$_{21}$F$_2$NO$_5$S) C, H, N, F, O, S.

2-methyl-5-[4-methylsulphonyl)phenyl]-1-(3,4-difluorophenyl)-1H-pyrrole

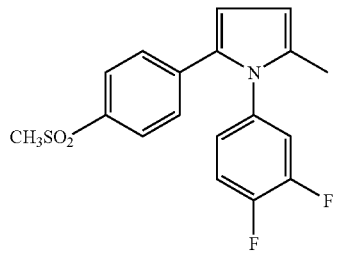

Prepared in 74% yield as reported in the literature (Biava et al., J. Med. Chem., 2005, 48, 3428).

Example 3

Isopropyl[1-(4-methoxy)phenyl-2-methyl-5-(4-methylsulphonyl)phenyl-1H-pyrrol-3-yl]acetate

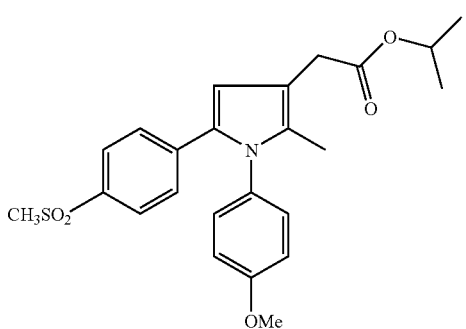

Prepared according to the procedure described in example 1, in 40% yield, starting from isopropyl-1-(4-methoxyphenyl)-2-methyl-5-[4-methylsulphonyl)phenyl]-1H-pyrrole-3-glyoxylate; Yellowish needles; Mp 138° C.; NMR (CDCl$_3$)

7.65-7.68 (d, 2H), 7.24-7.27 (d, 2H), 7.14-7.16 (d, 2H), 7.00-7.02 (d, 2H), 6.53 (s, 1H), 4.96 (m, 1H), 3.83-3.84 (s, 3H), 3.45 (s, 2H), 3.02-3.04 (s, 3H), 2.02-2.05 (s, 3H), 1.18-1.23 (d, 6H) Anal. ($C_{24}H_{27}NO_5S$) C, H, N, O, S.

Isopropyl 1-(4-methoxyphenyl)-2-methyl-5-[4-methylsulphonyl)phenyl]-1H-pyrrole-3-glyoxylate

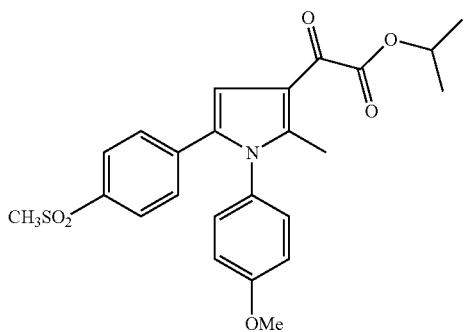

Prepared according to the procedure described in example 1, in 40% yield starting from 2-methyl-5-[4-methylsulphonyl)phenyl]-1-(4-methoxyphenyl)-1H-pyrrole, prepared according to literature (v.s.). Yellowish needles (yield 40%); Mp 124° C.; NMR (CDCl$_3$) 7.77-7.80 (d, 2H), 7.65-7.69 (m, 1H), 7.38-7.41 (d, 2H), 7.32-7.35 (d, 2H), 7.24-7.26 (d, 1H), 6.98-6.99 (s, 1H), 5.26 (m, 1H), 3.08-3.09 (s, 3H), 2.44-2.45 (s, 3H), 1.38-1.40 (d, 6H). Anal. ($C_{23}H_{22}FNO_5S$) C, H, N, O, S.

Example 4

Isopropyl[1-(3-fluoro)phenyl-2-methyl-5-(4-methylsulphonyl)phenyl-1H-pyrrol-3-yl]acetate

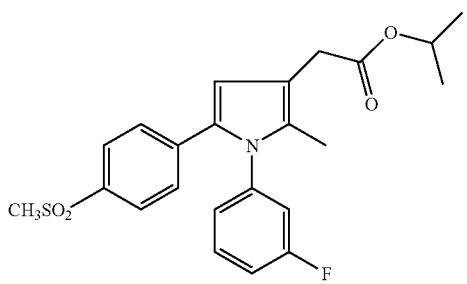

Prepared according to the procedure described in example 1, in 96% yield, starting from isopropyl-2-methyl-5-[4-methylsulphonyl)phenyl]-1-(3-fluorophenyl)-1H-pyrrole-3-glyoxylate. Yellowish needles; Mp 100° C.; NMR (CDCl$_3$) 7.71-7.75 (m, 2H), 7.52-7.56 (m, 1H), 7.10-7.15 (m, 3H), 7.09-7.10 (m, 2H), 6.55-6.57 (m, 1H), 4.96 (m, 1H), 3.46-3.47 (s, 2H), 2.80-2.83 (s, 3H), 2.04-2.09 (s, 3H), 1.20-1.24 (d, 6H). Anal. ($C_{23}H_{24}FNO_4S$) C, H, N, O, S.

Isopropyl-2-methyl-5-[4-methylsulphonyl)phenyl]-1-(3-fluoro-phenyl)-1H-pyrrole-3-glyoxylate

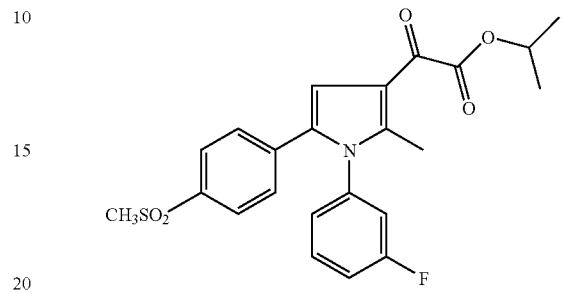

Prepared according to the procedure described in example 1, in 40% yield starting from 2-methyl-5-[4-methylsulphonyl)phenyl]-1-(3-fluorophenyl)-1H-pyrrole, prepared according to literature (v.s.). Yellowish needles (yield 40%); Mp 124° C.; NMR (CDCl$_3$) 7.77-7.80 (d, 2H), 7.65-7.69 (m, 1H), 7.38-7.41 (d, 2H), 7.32-7.35 (d, 2H), 7.24-7.26 (d, 1H), 6.98-6.99 (s, 1H), 5.26 (m, 1H), 3.08-3.09 (s, 3H), 2.44-2.45 (s, 3H), 1.38-1.40 (d, 6H). Anal. ($C_{23}H_{22}FNO_5S$) C, H, N, O, S.

Example 5 n-Butyl[1-(3,4-difluoro)phenyl-2-methyl-5-(4-methylsulphonyl)phenyl-1H-pyrrol-3-yl]acetate

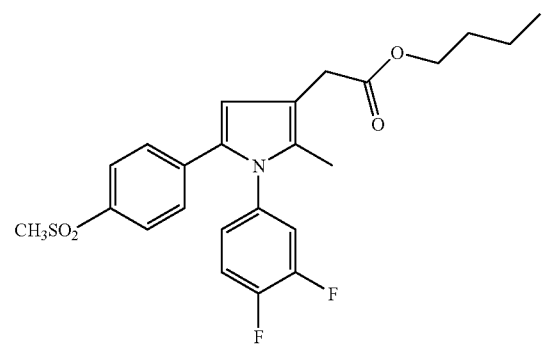

Prepared according to the procedure described in example 1, in 40% yield, starting from n-Butyl-2-methyl-5-[4-methylsulphonyl)phenyl]-1-(3,4-difluorophenyl)-1H-pyrrole-3-glyoxylate. Yellowish needles; Mp 112° C.; NMR (CDCl$_3$) 7.68-7.61 (d, 2H), 7.17-7.20 (s, 3H), 7.10-7.12 (d, 2H), 6.49-6.50 (s, 1H), 4.11-4.12 (t, 2H), 3.47-3.49 (s, 2H), 3.00-3.01 (s, 3H), 2.06-2.07 (s, 3H), 1.62-1.64 (t, 2H) 1.20-1.30 (m, 2H), 0.91-0.95 (t, 3H). Anal. (C$_{24}$H$_{26}$F$_2$NO$_4$S) C, H, N, F, O, S.

n-butyl-2-Methyl-5-[4-(methylsulphonyl)phenyl]-1-[3,4-(difluoro)phenyl]-1H-pyrrole-3-glyoxylate

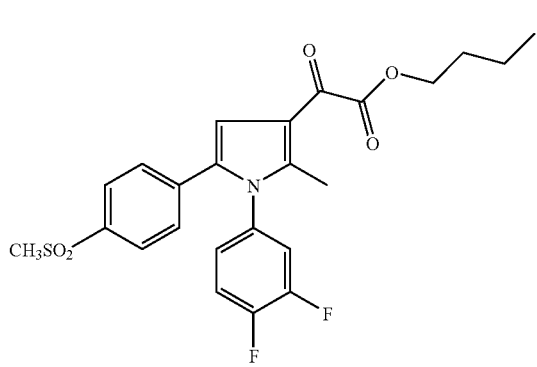

Prepared in 65% yield, according to the procedure described in example 1 but using n-butanol instead of isopropanol, starting from 2-methyl-5-[4-methylsulphonyl)phenyl]-1-(3,4-difluorophenyl)-1H-pyrrole, prepared according to literature (v.s.). Yellowish needles; Mp 45° C.; NMR (CDCl$_3$) 7.75-7.77 (d, 2H), 7.20-7.28 (s, 1H), 7.05-7.07 (d, 2H), 7.02-7.04 (m, 2H), 6.92-6.95 (s, 1H), 4.33-4.37 (t, 2H), 3.02 (s, 3H), 2.46 (s, 3H), 1.52-1.76 (q, 2H) 1.45-1.47 (m, 2H), 0.94-0.98 (t, 3H). Anal. (C$_{24}$H$_{23}$F$_2$NO$_5$S) C, H, N, F, O, S.

Example 6 n-Butyl[1-phenyl-2-methyl-5-(4-methylsulphonyl)phenyl-1H-pyrrol-3-yl]acetate

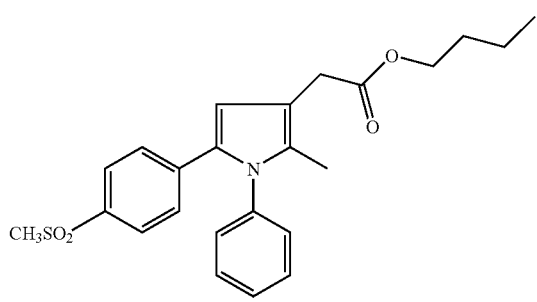

Prepared according to the procedure described in example 1, in 50% yield, starting from n-Butyl-2-methyl-5-[4-methylsulphonyl)phenyl]-1-phenyl)-1H-pyrrole-3-glyoxylate. Yellowish needles; Mp 124° C. NMR (CDCl$_3$) 7.66-7.68 (d, 2H), 7.48-7.50 (m, 5H), 7.23-7.26 (d, 2H), 6.56 (s, 1H), 4.08-4.09 (t, 2H), 3.51 (s, 2H), 3.04-3.05 (s, 3H), 2.04-2.06 (s, 3H), 1.13-1.15 (q, 2H) 1.12-1.13 (m, 2H), 0.90-0.92 (t, 3H). Anal. (C$_{24}$H$_{27}$NO$_4$S) C, H, N, O, S.

n-butyl-2-Methyl-5-[4-(methylsulphonyl)phenyl]-1-phenyl-1H-pyrrole-3-glyoxylate

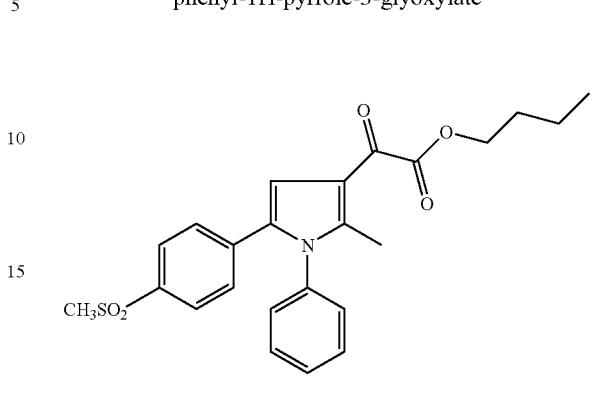

Prepared in 90% yield, according to the procedure described in example 1, but using n-butanol instead of isopropanol, starting from 2-methyl-5-[4-methylsulphonyl)phenyl]-1-phenyl-1H-pyrrole, prepared according to literature (v.s.). Yellowish needles; Mp 100° C. NMR (CDCl$_3$) 7.70-7.72 (d, 2H), 7.47-7.48 (m, 2H), 7.22-7.27 (m, 1H), 7.17-7.20 (d, 2H), 7.15-7.16 (m, 2H), 7.09-7.10 (s, 1H), 4.36-5.39 (t, 2H), 3.01 (s, 3H), 2.47 (s, 3H), 1.77-1.79 (q, 2H) 1.47-1.49 (m, 2H), 0.96-1.00 (t, 3H). Anal. (C$_{24}$H$_{25}$NO$_5$S) C, H, N, O, S.

Example 7

Ethyl[2-hydroxy-2-[2-methyl-5-(4-methylsulphonyl)phenyl-1-phenyl-1H-pyrrol-3-yl]]acetate

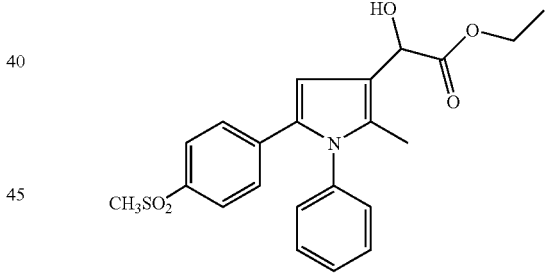

To a solution of ethyl-2-methyl-5-[4-methylsulphonyl)phenyl]-1-phenyl-1H-pyrrole-3-glyoxylate (1.46 mmol) in dichloromethane (CH$_2$Cl$_2$) (9 mL) stirred at r.t. was added ZnCl$_2$ (2.17 mmol). After 5 min sodiumcianoborohydride (1.08 mmol) was added, the mixture was left to react for 2 h under stirring at room temperature. At the end the mixture was added of tert-butyl alcohol and filtered on celite, the mixture was made acid with a solution of ammonium chloride (10%) in HCl 6N and extracted with CHCl$_3$. The organic solution was washed, dried and evaporated in vacuo. The resulting residue was chromatographed on silica gel eluting with ether/ethyle-acetate (1:1) to give a solid which after re-crystallization from acetate afforded the required product. Mp 145° C. (yield 50%); $^1$H NMR (CDCl$_3$) 7.62-7.67 (m, 2H), 7.24-7.27 (m, 3H), 7.12-7.17 (m, 4H), 6.47-6.50 (m, 1H), 5.21 (s, 1H), 4.24-4.37 (m, 2H), 3.20-3.22 (broad, 1H), 2.96-3.01 (s, 3H), 2.13-2.18 (s, 3H), 1.28-1.35 (t, 3H). Anal. (C$_{22}$H$_{23}$NO$_5$S) C, H, N.

Ethyl-2-methyl-5-[4-methylsulphonyl)phenyl]-1-phenyl-1H-pyrrole-3-glyoxylate was prepared as reported by the literature (Biava et al., J. Med. Chem., 2005, 48, 3428).

Enantiomers of the compound described in example 7 are separated by chromatography, using a Chiral Pack IA, chiral stationary phase, using a n-hexane:dichloromethane:ethanol (50:50:1) as eluant.

Example 7a (+)Ethyl[2-hydroxy-2-[2-methyl-5-(4-methylsulphonyl)phenyl-1-phenyl-1H-pyrrol-3-yl]]acetate $[\alpha]_D$=+70° (c=0.049, EtOH).

Example 7b (−)Ethyl[2-hydroxy-2-[2-methyl-5-(4-methylsulphonyl)phenyl-1-phenyl-1H-pyrrol-3-yl]]acetate $[\alpha]_D$=−60° (c=0.049, EtOH).

Example 8

Ethyl[2-hydroxy-2-[1-(4-methoxy)phenyl-2-methyl-5-(4-methylsulphonyl)phenyl-1H-pyrrol-3-yl]]acetate Enantiomers of the compound described in example 8 are separated by chromatography, using a Chiral Pack IA, chiral stationary phase, using a n-hexane:dichloromethane:ethanol (50:50:1) as eluant.

Example 8a (+)-Ethyl[2-hydroxy-2-[1-(4-methoxy)phenyl-2-methyl-5-(4-methylsulphonyl)phenyl-1H-pyrrol-3-yl]]acetate $[\alpha]_D$=+57° (c=0.086, EtOH).

Example 8b (−)-Ethyl[2-hydroxy-2-[1-(4-methoxy)phenyl-2-methyl-5-(4-methylsulphonyl)phenyl-1H-pyrrol-3-yl]]acetate $[\alpha]_D$=−58° (c=0.091, EtOH).

Example 9

Ethyl[2-hydroxy-2-[1-(3-fluoro)phenyl-2-methyl-5-(4-methylsulphonyl)phenyl-1H-pyrrol-3-yl]]acetate

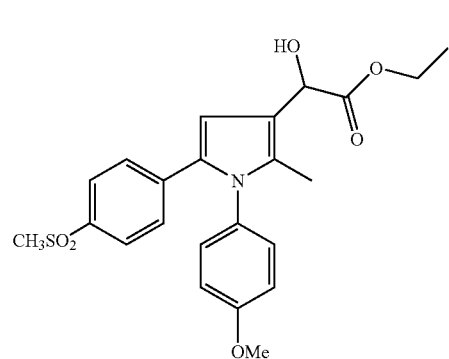

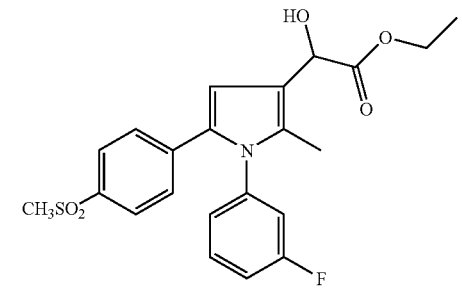

Prepared in 60% yield, as described in Example 7 and starting from ethyl-2-methyl-5-[4-methylsulphonyl)phenyl]-1-(4-methoxyphenyl)-1H-pyrrole-3-glyoxylate. Mp 130° C.; $^1$H NMR (CDCl$_3$): 7.65-7.67 (d, 2H), 7.16-7.18 (d, 2H), 7.12-7.15 (m, 2H), 7.06-7.11 (m, 2H), 6.46 (s, 1H), 5.02 (s, 1H), 4.19 (m, 2H), 3.85 (s, 3H), 3.20-3.25 (broad, 1H), 3.00 (s, 3H), 2.14 (s, 3H), 1.29-133 (t, 3H). Anal. (C$_{23}$H$_{25}$NO$_6$S) C, H, N.

Prepared in 55% yield, as described in Example 7, starting from ethyl-[1-(3-fluoro)phenyl-2-methyl-5-(4-methylsulphonyl)phenyl-1H-pyrrol-3-yl]]glyoxylate. 173° C.; $^1$H NMR (CDCl$_3$): 7.66-7.72 (d, 2H), 7.37-7.38 (m, 1H), 7.24-7.25 (d, 2H), 6.90-6.93 (m, 3H), 6.46-6.47 (s, 1H), 5.18 (s, 1H), 4.22-4.35 (m, 2H), 2.99-3.20 (broad, 1 H) 2.98 (s, 3H), 2.15 (s, 3H), 1.24-1.32 (m, 3H). Anal. (C$_{22}$H$_{22}$FNO$_5$S) C, H, N.

Enantiomers of the compound described in example 9 are separated by chromatography, using a Chiral Pack IA, chiral stationary phase, using a n-hexane:dichloromethane:ethanol (50:50:1) as eluant.

Example 9a (+)-Ethyl[2-hydroxy-2-[1-(3-fluoro)phenyl-2-methyl-5-(4-methylsulphonyl)phenyl-1H-pyrrol-3-yl]]acetate $[\alpha]_D$=+88° (c=0.019, EtOH).

Example 9b (−)-Ethyl[2-hydroxy-2-[1-(3-fluoro)phenyl-2-methyl-5-(4-methylsulphonyl)phenyl-1H-pyrrol-3-yl]]acetate $[\alpha]_D$=−81° (c=0.046, EtOH).

Example 10

Ethyl[2-ethoxy-2-[-2-methyl-5-(4-methylsulphonyl)phenyl-1-phenyl-1H-pyrrol-3-yl]]acetate

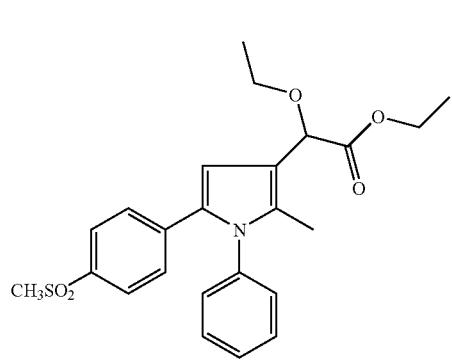

Prepared in 50% yield as described in example 7, but adding ethanol instead of t-butanol. Mp 165° C.; $^1$H NMR (CDCl$_3$) 7.62-7.64 (m, 2H), 7.24-7.27 (m, 3H), 7.12-7.15 (m, 4H), 6.47-6.60 (m, 1H), 4.92 (s, 1H), 4.15-4.40 (m, 2H), 3.50-3.70 (m, 2H), 2.97-3.00 (s, 3H), 2.13-2.18 (s, 3H), 1.28-1.32 (t, 6H). Anal. (C$_{24}$H$_{27}$NO$_5$S) C, H, N.

Enantiomers of the compound described in example 10 are separated by chromatography, using a Chiral Pack IA, chiral stationary phase, using a n-hexane:ethyleacetate:ethanol (75:25:0.2) as eluant.

Example 10a (+)-Ethyl[2-ethoxy-2-[-2-methyl-5-(4-methylsulphonyl)phenyl-1-phenyl-1H-pyrrol-3-yl]]acetate $[\alpha]_D$=+41° (c=0.027), EtOH).

Example 10b (−)-Ethyl[2-ethoxy-2-[-2-methyl-5-(4-methylsulphonyl)phenyl-1-phenyl-1H-pyrrol-3-yl]]acetate $[\alpha]_D$=−52° (c=0.022), EtOH).

Example 11

Ethyl[2-ethoxy-2-[1-(4-methoxy)phenyl-2-methyl-5-(4-methylsulphonyl)phenyl-1H-pyrrol-3-yl]]acetate

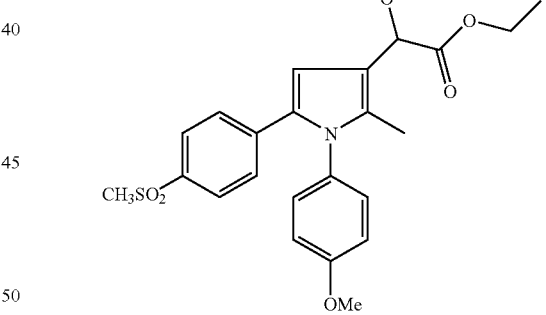

Prepared in 50% yield starting from Ethyl[2-[1-(4-methoxy)phenyl-2-methyl-5-(4-methylsulphonyl)phenyl-1H-pyrrol-3-yl]]glyoxylate, as described in example 7, but adding ethanol instead of t-butanol. Mp 159° C.; $^1$H NMR (CDCl$_3$): 7.65-7.67 (d, 2H), 7.14-7.16 (d, 2H), 7.04-7.08 (m, 2H), 6.88-6.90 (m, 2H), 6.56 (s, 1H), 4.89-490 (s, 1H), 4.18-4.28 (m, 2H), 3.77-3.83 (s, 3H), 3.56-3.65 (m, 2H), 2.92-2.98 (s, 3H), 2.14 (s, 3H), 1.23-131 (t, 6H). Anal. (C$_{25}$H$_{29}$NO$_6$S) C, H, N.

Enantiomers of the compound described in example 11 are separated by chromatography, using a Chiral Pack IA, chiral stationary phase, using a n-hexane:ethyleacetate:ethanol (75:25:0.2) as eluant.

Example 11a (+)-Ethyl[2-ethoxy-2-[1-(4-methoxy)phenyl-2-methyl-5-(4-methyl sulphonyl)phenyl-1H-pyrrol-3-yl]]acetate $[\alpha]_D$=+32° (c=0.040), EtOH.

Example 11b (−)-Ethyl[2-ethoxy-2-[1-(4-methoxy)phenyl-2-methyl-5-(4-methyl sulphonyl)phenyl-1H-pyrrol-3-yl]]acetate $[\alpha]_D$=−43° (c=0.043), EtOH.

Example 12

Ethyl[2-ethoxy-2-[1-(3-fluoro)phenyl-2-methyl-5-(4-methylsulphonyl)phenyl-1H-pyrrol-3-yl]]acetate Prepared in 55% yield starting from Ethyl[2-[1-(3-fluoro)phenyl-2-methyl-5-(4-methylsulphonyl)phenyl-1H-pyrrol-3-yl]]-glyoxylate, as described in example 7, but adding ethanol instead of t-butanol. Mp 165° C.; $^1$H NMR (CDCl$_3$): 7.66-7.72 (d, 2H), 7.37-7.38 (m, 1H), 7.23-7.25 (d, 2H), 6.90-6.93 (m, 3H), 6.55-6.57 (s, 1H), 4.79-4.82 (s, 1H), 4.23-4.27 (m, 2H), 3.43-3.45 (m, 2H) 2.96-3.00 (s, 3H), 2.16 (s, 3H), 1.28-1.32 (t, 6H). Anal. (C$_{24}$H$_{26}$FNO$_5$S) C, H, N.

Enantiomers of the compound described in example 12 are separated by chromatography, using a Chiral Pack IA, chiral stationary phase, using a n-hexane:ethyleacetate:ethanol (75:25:0.2) as eluant.

Example 12a (+)-Ethyl[2-ethoxy-2-[1-(3-fluoro)phenyl-2-methyl-5-(4-methylsulphonyl)phenyl-1H-pyrrol-3-yl]]acetate $[\alpha]_D$=+45° (c=0.041), EtOH.

Example 12b (−)-Ethyl[2-ethoxy-2-[1-(3-fluoro)phenyl-2-methyl-5-(4-methyl sulphonyl)phenyl-1H-pyrrol-3-yl]]acetate $[\alpha]_D$=−34° (c=0.020), EtOH.

Example 13

N-Methyl-[2-methyl-5-(4-methylsulphonyl)phenyl-1-phenyl-1H-pyrrol-3-yl]acetamide

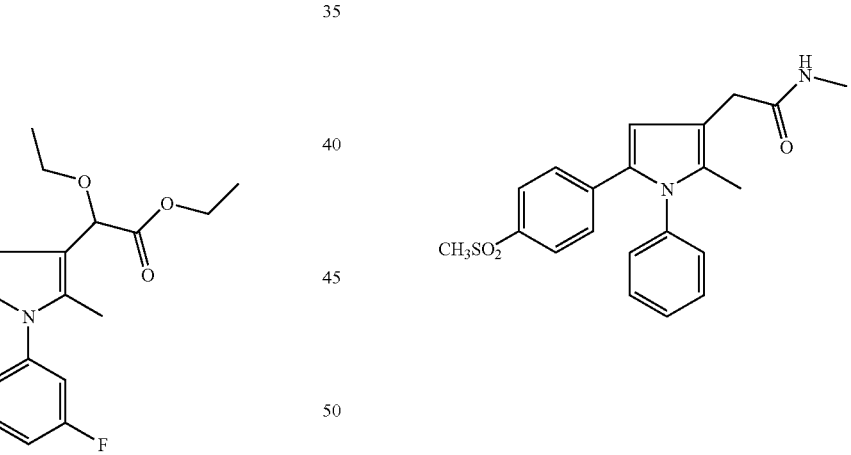

A solution of HOBt (0.3 mmol) in dry dichloromethane (5 mL) was added to a cold (0-5° C.) solution of [2-methyl-5-(4-methylsulphonyl)phenyl-1-phenyl-1H-pyrrol-3-yl]acetic acid (0.3 mmol)(Biava et al., J. Med. Chem., 2005, 48, 3428), and methylamine (0.4 mmol) in the same solvent (15 mL). After 30 min, a solution of EDC (0.4 mmol) in dichloromethane (5 mL) was added dropwise, and the mixture was kept at r.t. for 5 h. The solution was washed successively with 2N HCl, saturated NaHCO$_3$ solution, and H$_2$O and then dried, and the solvent was evaporated in vacuo.

The residue purified by flash-chromatography with EtOAc, to provide the required product. Yellowish needles from EtOAc Mp 178-181° C. (yield 77%) $^1$H-NMR (CDCl$_3$) δ ppm: 2.02 (s, 3H), 2.78 (d, 3H, J=4.8), 2.95 (s, 3H), 3.43 (s, 2H), 5.93 (br s, 1H), 6.43 (s, 1H), 7.10-7.15 (m, 4H), 7.34-7.42 (m, 3H), 7.61 (m, 2H). MS-ESI: m/z 383 (M+H⁺).

Example 14

N-Ethyl-[2-methyl-5-(4-methylsulphonyl)phenyl-1-phenyl-1H-pyrrol-3-yl]acetamide

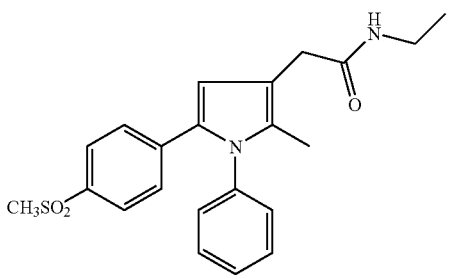

Prepared analogously to the procedure reported in example 13, in 70% yield using ethylamine.

Yellow oil ¹H-NMR (CDCl₃) δ ppm: 1.07 (t, 3H, J=7.1), 2.01 (s, 3H), 2.94 (s, 3H), 3.19-3.33 (m, 2H), 3.41 (s, 2H), 5.89 (br s, 1H), 6.42 (s, 1H), 7.09-7.13 (m, 4H), 7.37 (m, 3H), 7.61 (m, 2H). MS-ESI: m/z 419 (M+Na⁺).

Example 15

N,N-Dimethyl-[2-methyl-5-(4-methylsulphonyl)phenyl-1-phenyl-1H-pyrrol-3-yl]acetamide

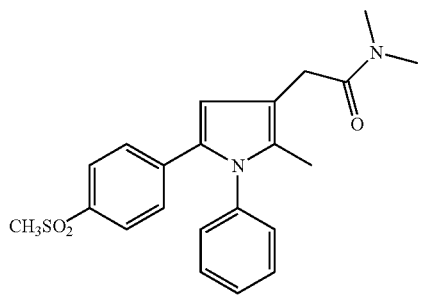

Prepared analogously to the procedure reported in example 13, in 70% yield using dimethylamine.

Yellowish needles from EtOAc/hexanes Mp 175-179° C. (yield 70%) ¹H-NMR (CDCl₃) δ ppm: 2.05 (s, 3H), 2.95 (s, 6H), 3.09 (s, 3H), 3.54 (s, 2H), 6.64 (s, 1H), 7.12 (m, 4H), 7.35-7.40 (m, 3H), 7.60 (m, 2H). MS-ESI: m/z 419 (M+Na⁺).

Example 16

N-Benzyl-N-methyl-[2-methyl-5-(4-methylsulphonyl)phenyl-1-phenyl-1H-pyrrol-3-yl]acetamide

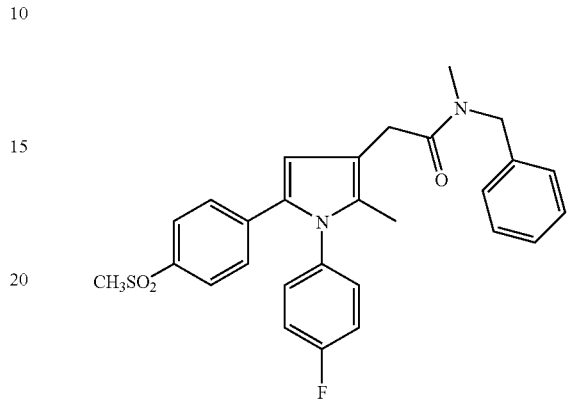

Prepared analogously to the procedure reported in example 13, in 86% yield from N-methyl-N-benzylamine and [2-methyl-5-(4-methylsulphonyl)phenyl-1-phenyl-1H-pyrrol-3-yl]acetic acid) (Biava et al., J. Med. Chem., 2005, 48, 3428). Purified with EtOAc/hexane (7:3 v/v) as eluant. Orange oil. The ¹H-NMR (CDCl₃) spectra show the presence of two different rotamers in equilibrium, for the sake of simplification the integral have not been given, δ ppm: 1.96 (s), 2.06 (s), 3.01 (m), 3.61 (s), 4.62 (s), 6.48 (s), 7.04-7.18 (m), 7.25-7.38 (m), 7.61 (m). MS-ESI: m/z 473 (M+H⁺).

Example 17

N-Methyl-[2-methyl-5-(4-methylsulphonyl)phenyl-1-(4-trifluoromethyl)phenyl-1H-pyrrol-3-yl]acetamide

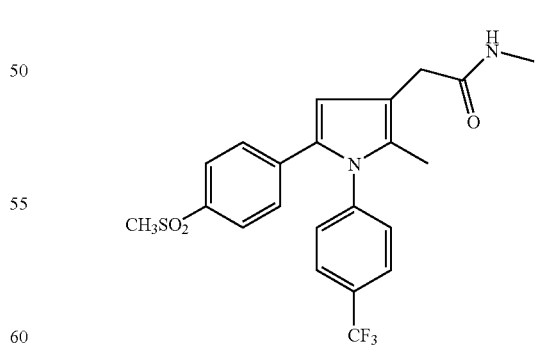

Prepared analogously to the procedure reported in example 13, in 71% yield from methylamine and [2-methyl-5-(4-methylsulphonyl)phenyl-1-(4-trifluoromethylphenyl)-1H-pyrrol-3-yl]acetic acid (prepared according to the literature, v.s.). Yellow oil. ¹H-NMR (CDCl₃) δ ppm: 2.06 (s, 3H), 2.80 (d, 3H, J=4.8), 2.99 (s, 3H), 3.44 (s, 2H), 5.87 (br s, 1H), 6.45 (s, 1H), 7.12 (m, 2H), 7.27 (m, 2H), 7.67 (m, 4H). MS-ESI: m/z 473 (M+Na$^+$).

Example 18

N-Ethyl-[2-methyl-5-(4-methylsulphonyl)phenyl-1-(4-trifluoromethyl)phenyl-1H-pyrrol-3-yl]acetamide

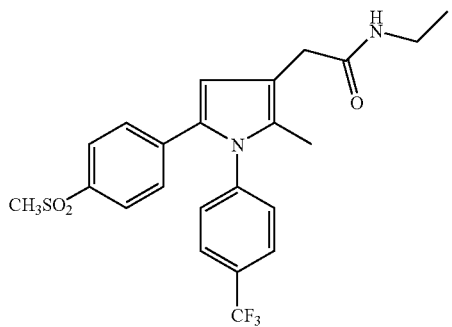

Prepared analogously to the procedure reported in example 13, in 69% yield from ethylamine and [2-methyl-5-(4-methylsulphonyl)phenyl-1-(4-trifluoromethylphenyl)-1H-pyrrol-3-yl]acetic acid. Orange oil $^1$H-NMR (CDCl$_3$) δ ppm: 1.11 (t, 3H, J=7.2), 2.06 (s, 3H), 2.99 (s, 3H), 3.22-3.36 (m, 2H), 3.42 (s, 2H), 5.79 (br s, 1H), 6.46 (s, 1H), 7.13 (m, 2H), 7.27 (m, 2H), 7.68 (m, 4H). MS-ESI: m/z 465 (M+H$^+$).

Example 19

N-Benzyl-N-methyl-[2-methyl-5-(4-methylsulphonyl)phenyl-1-(4-trifluoromethyl)phenyl-1H-pyrrol-3-yl]acetamide

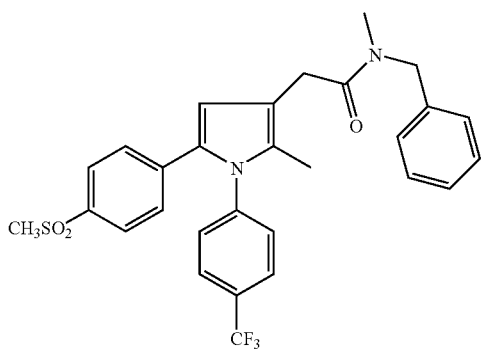

Prepared analogously to the procedure reported in example 13, in 77% yield from N-methyl-N-benzylamine and [2-methyl-5-(4-methylsulphonyl)phenyl-1-(4-trifluoromethylphenyl)-1H-pyrrol-3-yl]acetic acid. Purified with EtOAc/hexane (7:3 v/v) as eluant. Orange oil. The $^1$H-NMR (CDCl$_3$) spectra show the presence of two different rotamers in equilibrium, for the sake of simplification the integral have not been given, δ ppm: 1.98 (s), 2.09 (s), 2.97-3.01 (m), 3.61 (s), 4.63 (s), 6.49 (d), 7.06-7.16 (m), 7.25-7.32 (m), 7.61-7.68 (m).

Example 20

[2-Methyl-5-(4-methylsulphonyl)phenyl-3-(2-methoxyethyl)-1-phenyl]-1H-pyrrole

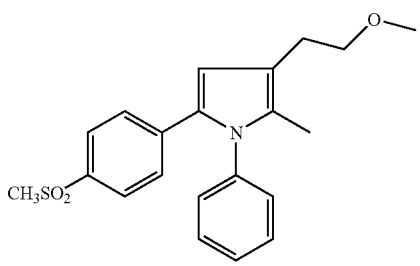

A suspension of powdered KOH (0.7 mmol) in DMSO (2 mL) was stirred for 5 min.

3-(2-Hydroxyethyl)-2-methyl-1-phenyl-5-[4-methylsulphonyl)phenyl]-1H-pyrrole (0.2 mmol) and methyl iodide (0.3 mmol) were added in sequence and the mixture after being stirred for additional 30 min was poured into water and extracted with dichloromethane. The organic extracts were washed with water, dried over Na$_2$SO$_4$ and evaporated to dryness in vacuo. The residue, purified by flash-chromatography (EtOAc/hexane 4:6 v/v), gave the titled compound as an oil. Light yellow oil (yield 45%) $^1$H-NMR (CDCl$_3$) δ ppm: 2.05 (s, 3H), 2.75 (t, 2H, J=7.1), 2.97 (s, 3H), 3.40 (s, 3H), 3.60 (t, 2H, J=7.3), 6.45 (s, 1H), 7.13 (m, 4H), 7.38 (m, 3H), 7.61 (m, 2H). MS-ESI: m/z 392 (M+Na$^+$).

3-(2-Hydroxyethyl)-2-methyl-1-phenyl-5-[4-methylsulphonyl)phenyl]-1H-pyrrole

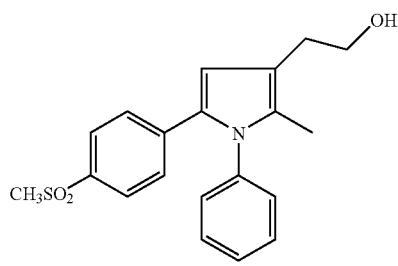

A solution of ethyl-[2-methyl-5-(4-methylsulphonyl)phenyl-1-phenyl-1H-pyrrol-3-yl]acetate (1.3 mmol) in dry THF (5 mL) was added dropwise to a stirred suspension of lithium aluminium hydride (2.8 mmol) in dry THF (20 mL). After stirring under N$_2$ atmosphere for 20 min, the excess of reducing agent was decomposed by careful addition of H$_2$O. The inorganic material was filtered off and washed with THF. The filtrate was dried (Na$_2$SO$_4$) and evaporated under reduced pressure. The residue, purified by flash-chromatography (EtOAc/hexane 6:4 v/v), gave the expected product.

Yellowish needles from EtOAc Mp 141-144° C. (yield 71%) $^1$H-NMR (CDCl$_3$) δ ppm: 2.07 (s, 3H), 2.77 (t, 2H, J=6.3), 2.98 (s, 3H), 3.85 (t, 2H, J=6.3), 6.46 (s, 1H), 7.13-7.17 (m, 4H), 7.40 (m, 3H), 7.64 (m, 2H).

Example 21

[3-(2-Ethoxyethyl)-2-methyl-5-(4-methylsulphonyl)phenyl-1-phenyl]-1H-pyrrole

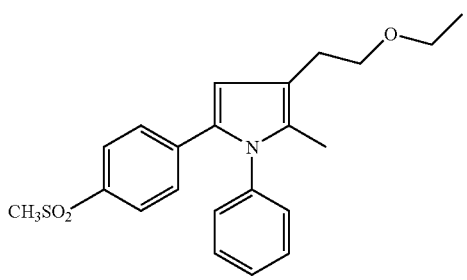

Prepared analogously to the procedure reported in example 20, in 48% yield using ethyl iodide instead of methyl iodide. Light yellow oil $^1$H-NMR (CDCl$_3$) δ ppm: 1.24 (t, 3H, J=7.0), 2.06 (s, 3H), 2.78 (t, 2H, J=7.4), 2.98 (s, 3H), 3.51-3.67 (m, 4H), 6.45 (s, 1H), 7.14 (m, 4H), 7.40 (m, 3H), 7.62 (m, 2H). MS-ESI: m/z 406 (M+Na$^+$).

Example 22

[2-Methyl-5-(4-methylsulphonyl)phenyl-1-phenyl-3-(2-n-propyloxyethyl)]-1H-pyrrole

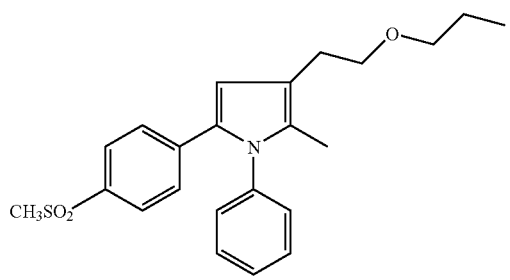

Prepared analogously to the procedure reported in example 20, in 46% yield using propyl iodide instead of methyl iodide. Light yellow oil $^1$H-NMR (CDCl$_3$) δ ppm: 0.93 (t, 3H, J=7.4), 1.57-1.67 (m, 2H), 2.05 (s, 3H), 2.76 (t, 2H, J=7.4), 2.97 (s, 3H), 3.44 (t, 2H, J=6.8), 3.62 (t, 2H, J=7.4), 6.45 (s, 1H), 7.13 (m, 4H), 7.37 (m, 3H), 7.61 (m, 2H). MS-ESI: m/z 420 (M+Na$^+$).

Example 23

[1-(4-Fluoro)phenyl-2-methyl-5-(4-methylsulphonyl)phenyl-3-(2-methoxyethyl)]-1H-pyrrole

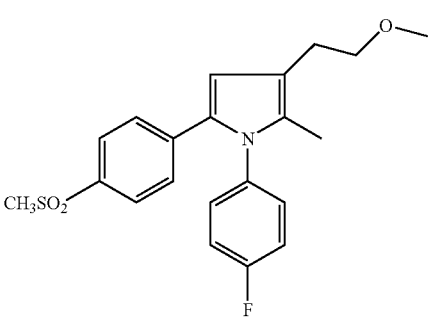

Prepared analogously to the procedure reported in example 20, in 58% yield from 1-(4-Fluoro)phenyl-3-(2-hydroxyethyl)-2-methyl-5-[4-methylsulphonyl)phenyl]-1H-pyrrole and methyl iodide. Light yellow oil $^1$H-NMR (CDCl$_3$) δ ppm: 2.04 (s, 3H), 2.75 (t, 2H, J=7.1), 2.99 (s, 3H), 3.40 (s, 3H), 3.60 (t, 2H, J=7.3), 6.44 (s, 1H), 7.03-7.16 (m, 6H), 7.65 (m, 2H). MS-ESI: m/z 409 (M+Na$^+$).

1-(4-Fluoro)phenyl-3-(2-hydroxyethyl)-2-methyl-5-[4-methylsulphonyl)phenyl]-1H-pyrrole

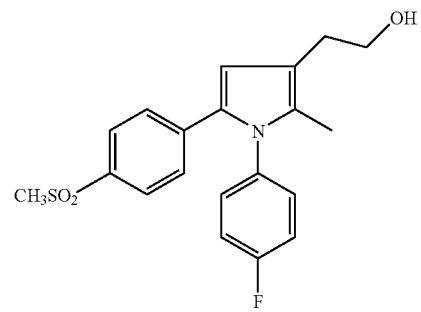

Prepared in 80% yield, as described in example 20 but by reducing ethyl-[2-methyl-5-(4-methylsulphonyl)phenyl-1-(4-Fluoro)phenyl-1H-pyrrol-3-yl]acetate. Yellow oil $^1$H-NMR (CDCl$_3$) δ ppm: 2.05 (s, 3H), 2.75 (t, 2H, J=6.5), 2.99 (s, 3H), 3.84 (t, 2H, J=6.5), 6.44 (s, 1H), 7.08-7.17 (m, 6H), 7.66 (m, 2H).

Example 24

[3-(2-Ethoxyethyl)-1-(4-Fluoro)phenyl-2-methyl-5-(4-methylsulphonyl)phenyl]-1H-pyrrole

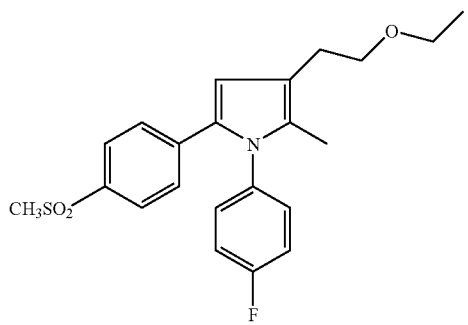

Prepared analogously to example 23, in 40% yield from ethyl iodide. Light yellow oil $^1$H-NMR (CDCl$_3$) δ ppm: 1.22 (t, 3H, J=6.9), 2.03 (s, 3H), 2.75 (t, 2H, J=7.4), 2.98 (s, 3H), 3.49-3.65 (m, 4H), 6.43 (s, 1H), 7.01-7.15 (m, 6H), 7.64 (m, 2H). MS-ESI: m/z 424 (M+Na$^+$).

Example 25

[1-(4-Fluoro)phenyl-2-methyl-5-(4-methylsulphonyl)phenyl-3-(2-n-propyloxyethyl)]-1H-pyrrole

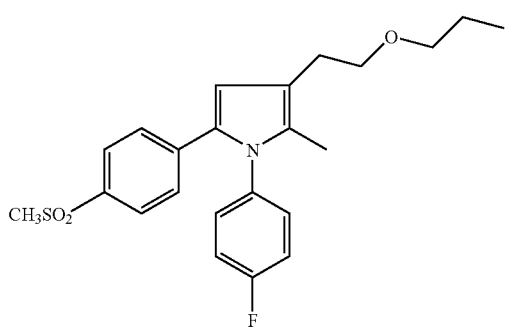

Prepared analogously to example 23, in 45% yield from propyl iodide. Light yellow oil $^1$H-NMR (CDCl$_3$) δ ppm: 0.93 (t, 3H, J=7.4), 1.56-1.67 (m, 2H), 2.03 (s, 3H), 2.75 (t, 2H, J=7.3), 2.98 (s, 3H), 3.44 (t, 2H, J=6.8), 3.61 (t, 2H, J=7.3), 6.44 (s, 1H), 7.04-7.15 (m, 6H), 7.64 (m, 2H). MS-ESI: m/z 438 (M+Na$^+$).

Example 26

[2-Methyl-5-(4-methylsulphonyl)phenyl-3-(2-methoxyethyl)-1-(4-trifluoromethyl)phenyl]-1H-pyrrole

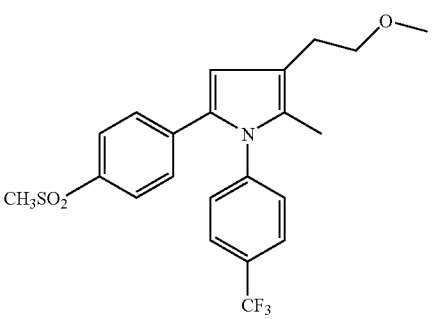

Prepared analogously to the procedure reported in example 20, in 52% yield from 1-[(4-trifluoromethylphenyl)-3-(2-hydroxyethyl)-2-methyl-5-[4-methylsulphonyl)phenyl]-1H-pyrrole and methyl iodide. Light yellow oil. $^1$H-NMR (CDCl$_3$) δ ppm: 2.07 (s, 3H), 2.76 (t, 2H, J=7.0), 3.00 (s, 3H), 3.40 (s, 3H), 3.60 (t, 2H, J=6.7), 6.47 (s, 1H), 7.13 (m, 2H), 7.26 (m, 2H), 7.67 (m, 4H). MS-ESI: m/z 459 (M+Na$^+$).

3-(2-Hydroxyethyl)-2-methyl-5-[4-methylsulphonyl)phenyl-1-(4-trifluoromethyl)phenyl]-1H-pyrrole

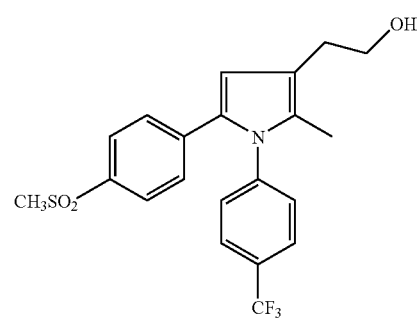

Prepared analogously to the procedure reported in example 20, in 71% yield, from ethyl 1[2-methyl-5-(4-methylsulphonyl)phenyl-(4-trifluoromethyl)phenyl-1H-pyrrole-3-yl]acetate and methyl iodide. Yellow oil $^1$H-NMR (CDCl$_3$) δ ppm:

2.07 (s, 3H), 2.74 (t, 2H, J=6.5), 2.98 (s, 3H), 3.83 (t, 2H, J=6.5), 6.46 (s, 1H), 7.12 (m, 2H), 7.26 (m, 2H), 7.66 (m, 4H).

Example 27

[3-(2-Ethoxyethyl)-2-methyl-5-(4-methylsulphonyl) phenyl-1-(4-trifluoromethyl)phenyl]-1H-pyrrole

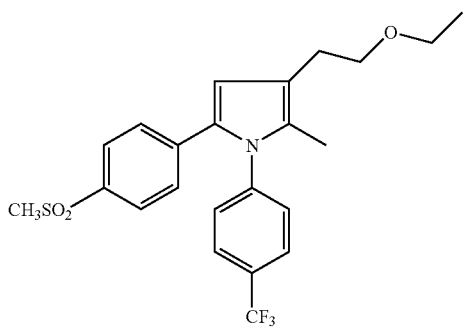

Prepared analogously to example 26, in 48% yield using ethyl iodide instead of methyl iodide. Light yellow oil. $^1$H-NMR (CDCl$_3$) δ ppm: 1.22 (t, 3H, J=6.9), 2.07 (s, 3H), 2.76 (t, 2H, J=7.2), 2.99 (s, 3H), 3.49-3.65 (m, 4H), 6.45 (s, 1H), 7.11 (m, 2H), 7.25 (m, 2H), 7.66 (m, 4H). MS-ESI: m/z 474 (M+Na$^+$).

Example 28

[2-Methyl-5-(4-methylsulphonyl)phenyl-3-(2-n-propyloxyethyl)-1-(4-trifluoromethyl)phenyl]-1H-pyrrole

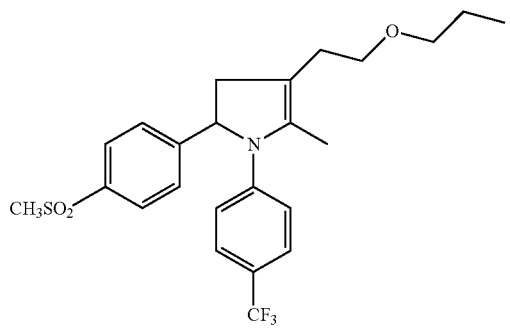

Prepared analogously to example 26, in 46% yield using propyl iodide instead of methyl iodide. Light yellow oil $^1$H-NMR (CDCl$_3$) δ ppm: 0.98 (t, 3H, J=7.4), 1.54-1.68 (m, 2H), 2.07 (s, 3H), 2.76 (t, 2H, J=7.1), 3.00 (s, 3H), 3.45 (t, 2H, J=6.7), 3.62 (t, 2H, J=7.2), 6.47 (s, 1H), 7.12 (m, 2H), 7.25 (m, 2H), 7.67 (m, 4H). MS-ESI: m/z 466 (M+H$^+$).

Example 29

2-(1-(4-Fluorophenyl)-2-methyl-5-(4-methylsulphonyl)phenyl-1H-pyrrol-3-yl)ethyl propionate

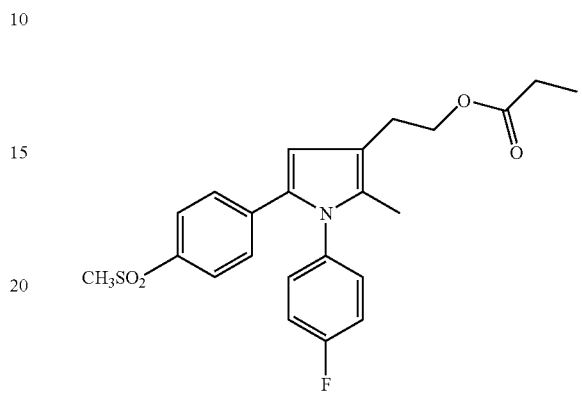

To a solution of 1-(4-Fluoro)phenyl-3-(2-hydroxyethyl)-2-methyl-5-[4-methylsulphonyl)phenyl]-1H-pyrrole (example 23) (0.28 mmol), in dry dichloromethane (20 mL) cooled at 0° C. and under an atmosphere of N$_2$, TEA (0.5 mL) was added and the mixture was stirred for 10 min. Then propionyl chloride (0.34 mmol) was added at 0° C., and the reaction was stirred for 30 min at r.t. The reaction mixture was washed with water, dried over Na$_2$SO$_4$ and evaporated to dryness in vacuo. The residue, purified by flash-chromatography (EtOAc/hexane 4:6 v/v), gave the expected compound, yellow oil (yield 72%) $^1$H-NMR (CDCl$_3$) δ ppm: 1.11 (t, 3H, J 7.1), 2.03 (s, 3H), 2.32 (q, 2H, J=7.2), 2.78 (t, 2H, J=7.3), 2.96 (s, 3H), 4.22 (t, 2H, J=7.1), 6.40 (s, 1H), 7.06-7.14 (m, 6H), 7.61-7.66 (m, 2H).

Example 30

2-(1-(4-fluorophenyl)-2-methyl-5-(4-methylsulphonyl)phenyl-1H-pyrrol-3-yl)ethyl butanoate

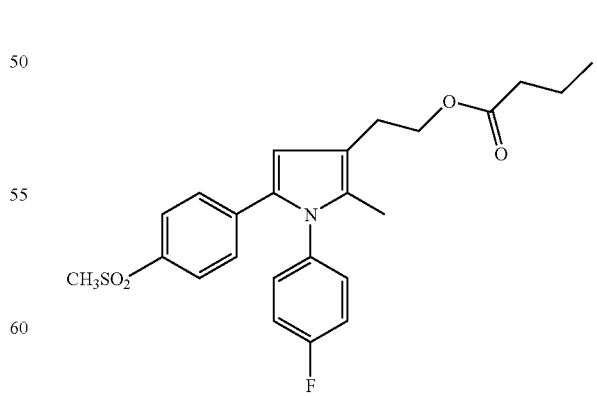

Prepared analogously to example 29, in 80% yield using butyrroyl chloride. Yellow oil. $^1$H-NMR (CDCl$_3$) δ ppm: 0.90 (t, 3H, J=7.1), 1.57-1.71 (m, 2H), 2.02 (s, 3H), 2.27 (t, 2H, J=7.2), 2.78 (t, 2H, J=7.1), 2.95 (s, 3H), 4.22 (t, 2H, J=7.3), 6.40 (s, 1H), 7.09 (m, 6H), 7.62 (m, 2H).

Example 31

2-(1-(4-fluorophenyl)-2-methyl-5-(4-methylsulphonyl)phenyl-1H-pyrrol-3-yl)ethyl benzoate

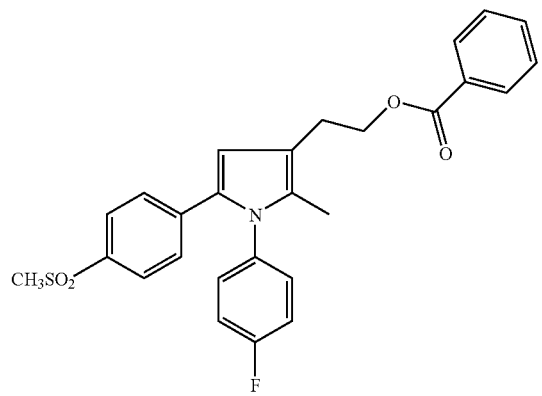

Prepared analogously to example 29, in 60% yield using benzoyl chloride. Yellow oil $^1$H-NMR (CDCl$_3$) δ ppm: 2.06 (s, 3H), 2.94 (m, 5H), 4.49 (t, 2H, J=7.1), 6.47 (s, 1H), 7.06-7.15 (m, 6H), 7.38-7.45 (m, 2H), 7.52 (m, 1H), 7.62-7.67 (m, 2H), 8.04 (m, 2H).

Example 32

2-(1-(4-fluorophenyl)-2-methyl-5-(4-methylsulphonyl)phenyl-1H-pyrrol-3-yl)ethyl 2-fluorobenzoate

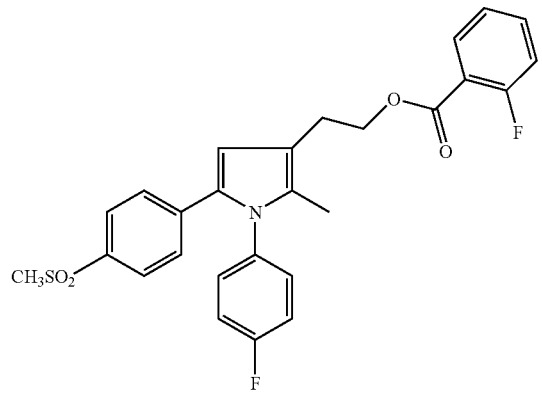

Prepared analogously to example 29, in 95% yield using 2-fluorobenzoyl chloride. Yellow oil. $^1$H-NMR (CDCl$_3$) δ ppm: 2.05 (s, 3H), 2.94 (m, 5H), 4.50 (t, 2H, J=7.04), 6.49 (s, 1H), 7.07-7.21 (m, 8H), 7.51 (m, 1H), 7.65 (m, 2H), 7.89-7.99 (m, 1H).

Example 33

2-(1-(4-fluorophenyl)-2-methyl-5-(4-methylsulphonyl)phenyl-1H-pyrrol-3-yl)ethyl 4-fluorobenzoate

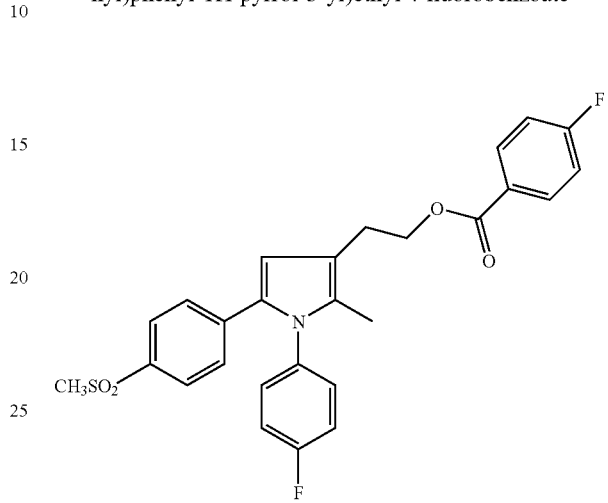

Prepared analogously to example 29, in 66% yield using 4-fluorobenzoyl chloride. Yellow oil. $^1$H-NMR (CDCl$_3$) δ ppm: 2.06 (s, 3H), 2.94 (m, 5H), 4.47 (t, 2H, J=7.1), 6.45 (s, 1H), 7.05-7.15 (m, 8H), 7.65 (m, 2H), 8.02-8.09 (m, 2H).

Example 34

2-(1-(4-fluorophenyl)-2-methyl-5-(4-methylsulphonyl)phenyl-1H-pyrrol-3-yl)ethyl 2-tiophencarboxylate

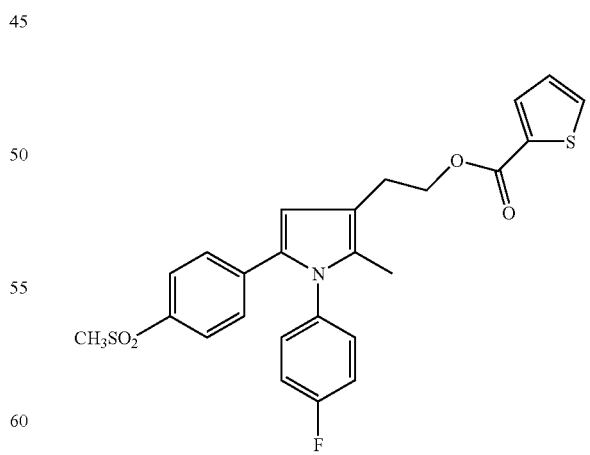

Prepared analogously to example 29, in 60% yield using 2-thienoyl chloride. Yellow oil $^1$H-NMR (CDCl$_3$) δ ppm:

2.07 (s, 3H), 2.93 (m, 5H), 4.45 (t, 2H, J=7.0), 6.47 (s, 1H), 7.02-7.15 (m, 7H), 7.54 (m, 1H), 7.63-7.67 (m, 2H), 7.80 (m, 1H).

Example 35

N-[2-[1-(4-Fluorophenyl)-2-methyl-5-(4-(methylsulphonyl)phenyl)-1H-pyrrol-3-yl]ethyl]benzamide

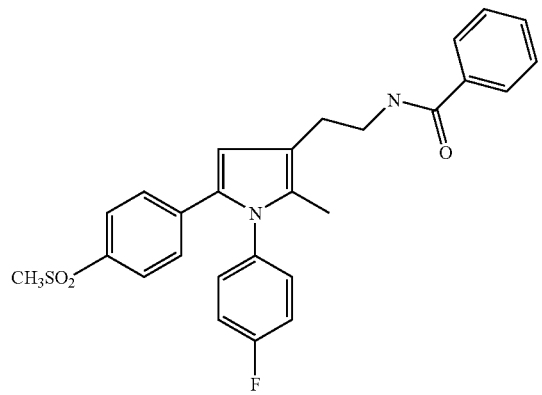

To a solution of 2-(1-(4-fluorophenyl)-2-methyl-5-(4-(methylsulphonyl)phenyl)-1H-pyrrol-3-yl)ethanamine (0.20 mmol) in dry DMF (10 mL) cooled at 0° C. and under an atmosphere of $N_2$, TEA (0.20 mmol) was added and the mixture was stirred for 10 min. Then benzoyl chloride (0.20 mmol) was added at 0° C., and the reaction was stirred for 24 h at r.t.; the reaction mixture was washed with water, dried over $Na_2SO_4$ and evaporated to dryness in vacuo. The residue, purified by flash-chromatography (EtOAc/hexane 7:3 v/v), gave the expected compound as yellow oil (yield 70%). $^1$H-NMR (CDCl$_3$) δ ppm: 2.03 (s, 3H), 2.80 (t, 2H, J=7.1), 2.97 (s, 3H), 3.67 (m, 2H), 6.43-6.48 (m, 2H), 7.10 (m, 6H), 7.34-7.46 (m, 3H), 7.64 (m, 2H), 7.75 (m, 2H).

3-(2-Aminoethyl)-1-(4-fluorophenyl)-2-methyl-5-[4-(methylsulphonyl)phenyl]-1H-pyrrole

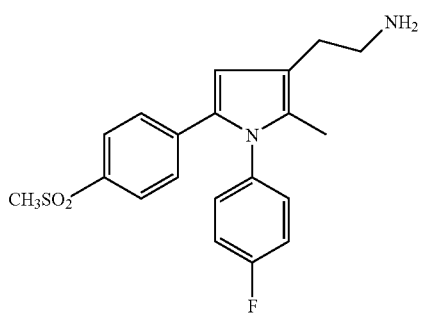

A suspension of phthalimido derivative (0.30 mmol) in MeOH (15 mL) treated with 98% hydrazine (3.00 mmol) was stirred at r.t. for 4 h. The mixture was concentrated under reduced pressure. The residue was partitioned between $CH_2Cl_2$ and an ice-cold aqueous dilute hydrochloric acid. The organic layer was discarded, and the acidic aqueous solution was made alkaline with ice-cold 3M sodium hydroxide solution. The reaction product was then extracted with $CH_2Cl_2$ and organic phase washed to neutrality with brine and dried over $Na_2SO_4$. Evaporation under reduced pressure gave the expected amine as a colorless oil (yield 70%) which was used as such in the next reaction.
$^1$H-NMR (DMSO-d$_6$) δ ppm: 1.97 (s, 3H), 2.72 (m, 2H), 2.96 (m, 2H), 3.11 (s, 3H), 6.54 (s, 1H), 7.14-7.29 (m, 6H), 7.66 (m, 2H), 7.87 (br s, 2H).

3-(2-phthalimidoethyl)-1-(4-fluorophenyl)-2-methyl-5-[4-(methylsulphonyl)phenyl]-1H-pyrrole

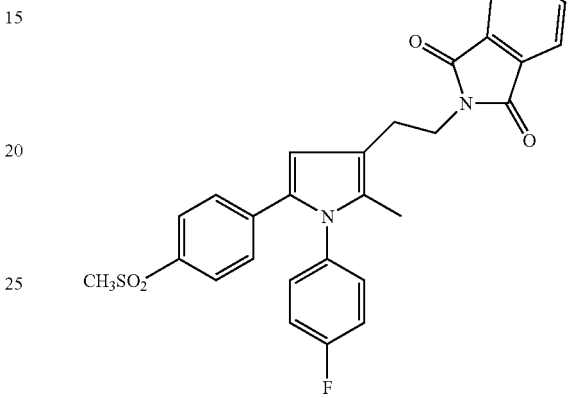

To a solution of 3-(2-bromoethyl)-1-(4-fluorophenyl)-2-methyl-5-[4-(methylsulphonyl)phenyl]-1H-pyrrole (0.80 mmol) in dry DMF (10 mL) was added sodium iodide (0.80 mmol) and the resulting mixture was stirred at r.t. for 30 min. Potassium phthalimide (0.90 mmol) was then added, and the reaction mixture was heated at 70° C. for 14 h. After cooling the mixture was poured onto crushed ice and extracted with $CH_2Cl_2$. The organic phase was thoroughly washed with water to remove the DMF excess, dried and concentrated under reduced pressure. The residue, purified by flash-chromatography (EtOAc/hexane 1:1 v/v), gave the expected compound as an oil which crystallizes on standing. Yellowish needles from EtOAc Mp 198-201° C. (yield 70%) $^1$H-NMR (CDCl$_3$) δ ppm: 2.04 (s, 3H), 2.86 (t, 2H, J=7.5), 2.98 (s, 3H), 3.88 (t, 2H, J=7.6), 6.42 (s, 1H), 7.07 (m, 6H), 7.61-7.74 (m, 4H), 7.81-7.85 (m, 2H).

3-(2-Bromoethyl)-1-(4-fluorophenyl)-2-methyl-5-[4-(methylsulphonyl)phenyl]-1H-pyrrole

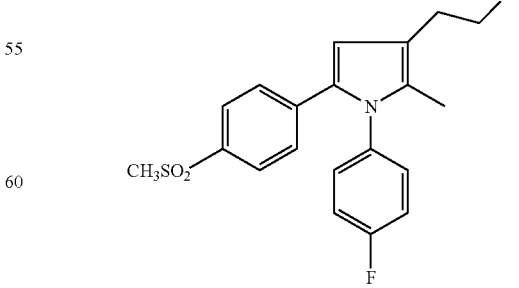

To a solution of 1-(4-fluoro)phenyl-3-(2-hydroxyethyl)-2-methyl-5-[4-methylsulphonyl)phenyl]-1H-pyrrole (example 23) (1.30 mmol) in CHCl₃, PBr₃ (5 mL) was added. The resulting mixture was stirred at r.t. for 2 h. The solution was cooled, the reaction quenched with ice, and the mixture basified with a saturated Na₂CO₃ solution and then extracted with CH₂Cl₂. The organic phase was washed to neutrality with brine, dried and evaporated under reduced pressure. The residue, purified by flash-chromatography (EtOAc/hexane 4:6 v/v), gave the expected compound as yellow oil (yield 36%) ¹H-NMR (CDCl₃) δ ppm: 2.03 (s, 3H), 2.96-3.06 (m, 5H), 3.52 (t, 2H, J=7.5), 6.41 (s, 1H), 7.05-7.15 (m, 6H), 7.61-7.66 (m, 2H).

Example 36

N-propyl-2-[-(2-Methyl-5-[4-(methylsulphonyl)phenyl]-1-phenyl-1H-pyrrol-3-yl)]ethyl propyl Carbamate

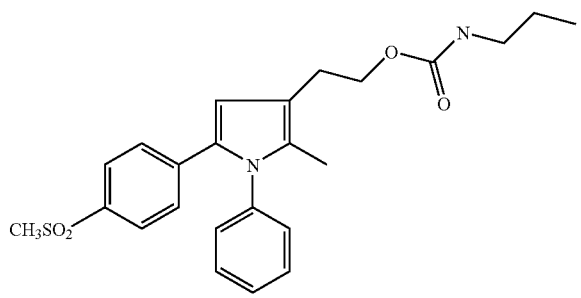

To a solution of 3-(2-Hydroxyethyl)-2-methyl-1-phenyl-5-[4-methylsulphonyl)phenyl]-1H-pyrrole (example 20) (0.41 mmol) in dry THF (10 mL), 1,1-carbonyldiimidazole (0.82 mmol) was added at 0° C. and the mixture stirred for 2 h at r.t. The solvent was removed in vacuo and the desiderate activated alcohol was obtained. To a stirred solution of activate alcohol in CH₃CN (8 mL), n-propylamine (0.61 mmol) and DMAP (0.61 mmol) were added at room temperature and the solution was stirred for 3 h. The reaction was hydrolysed with a saturated solution of NaHCO₃ and extracted with CH₂Cl₂. The organic layers were dried with Na₂SO₄ and evaporated to dryness in vacuo. The residue, purified by flash-chromatography (EtOAc/hexane 1:1 v/v), gave the expected compound as yellow oil (yield 85%). The ¹H-NMR (CDCl₃) spectra show the presence of two different rotamers in equilibrium, for the sake of simplification the integral have not been given, δ ppm: 0.85 (m), 1.43-1.50 (m), 2.02 (d), 2.76 (d), 2.92 (d), 3.08 (m), 4.19 (d), 4.88-4.93 (br d), 6.41 (d), 7.08 (m), 7.33 (m), 7.56-7.60 (m). MS-ESI: m/z 463.2 (M+Na⁺).

Example 37

2-(2-Methyl-5-[4-(methylsulphonyl)phenyl]-1-phenyl-1H-pyrrol-3-yl)ethyl propyl Carbonate

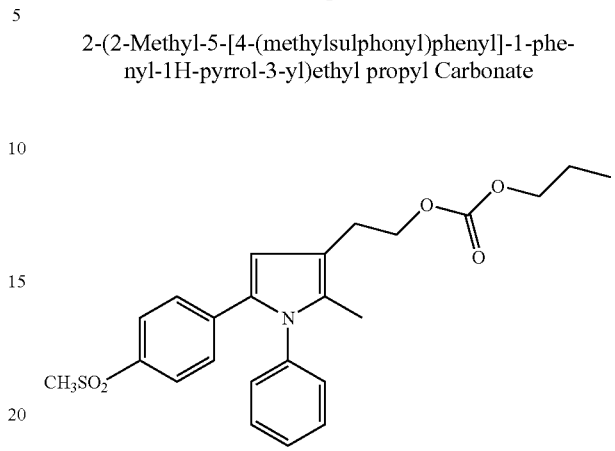

To a solution of 1-propanol (0.82 mmol) in dry THF (5 mL) at 0° C. 1,1-carbonyldiimidazole (1.02 mmol) was added. The solution was stirred at room temperature for 2 h and then added as such to a solution of 3-(2-Hydroxyethyl)-2-methyl-1-phenyl-5-[4-methylsulphonyl)phenyl]-1H-pyrrole (example 20) (0.41 mmol) in dry THF (10 mL) at 0° C., previously treated with NaH (0.41 mmol).

The mixture was stirred at 0° C. for 2 h. The solvent was removed under reduced pressure and the residue was dissolved in CH₂Cl₂ and washed with a saturated aqueous solution of NaCl, dried over Na₂SO₄ and evaporated to dryness in vacuo. The residue, purified by flash-chromatography (EtOAc/hexane 1:1 v/v), gave the expected compound as a yellow oil (yield 50%) ¹H-NMR (CDCl₃) δ ppm: 0.93 (t, 3H, J=7.1), 1.67 (m, 2H), 2.04 (s, 3H), 2.85 (t, 2H, J=7.2), 2.95 (s, 3H), 4.08 (t, 2H, J=6.9), 4.29 (t, 2H, J=7.3), 6.43 (s, 1H), 7.09-7.14 (m, 4H), 7.35-7.38 (m, 3H), 7.61 (m, 2H). MS-ESI: m/z 464.2 (M+Na⁺).

Example 38

Propyl-N-[2-[2-methyl-5-(4-(methylsulphonyl)phenyl)-1-phenyl-1H-pyrrol-3-yl]ethyl]carbamate

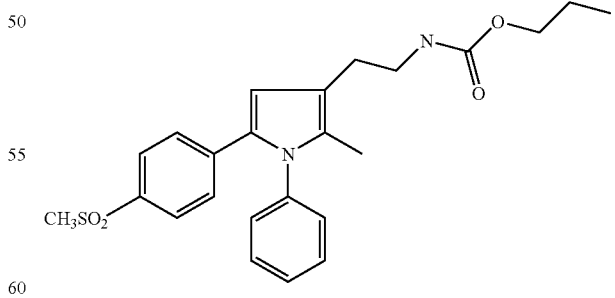

To a solution of 1-propanol (0.42 mmol) in dry CH₂Cl₂ (5 mL), 1,1-carbonyldiimidazole (0.51 mmol) was added at 0° C. and the mixture stirred for 4 h at r.t. The solvent was removed in vacuo and the respective activated alcohol was obtained. To a stirred solution of the activate alcohol in CH₃CN (8 mL), 2-(2-methyl-5-(4-(methylsulphonyl)phenyl)-1-phenyl-1H-pyrrol-3-yl)ethylamine (0.17 mmol) and DMAP (0.34 mmol) were added at r.t. and the solution was stirred for 24 h. The reaction mixture was treated with a saturated solution of $NaHCO_3$ and extracted with $CH_2Cl_2$. The organic layers were dried with $Na_2SO_4$ and evaporated to dryness in vacuo. The residue was purified by flash-chromatography (EtOAc/hexane 7:3 v/v) to afford the titled compound as a colorless oil (yield 70%).

$^1$H-NMR (CDCl$_3$) δ ppm: 0.90 (m, 3H), 1.60 (m, 2H), 2.03 (s, 3H), 2.67 (m, 2H), 2.96 (s, 3H), 3.39 (m, 2H), 4.00 (m, 2H), 4.86 (br s, 1H), 6.40 (s, 1H), 7.12 (m, 4H), 7.36-7.40 (m, 3H), 7.61 (m, 2H). MS-ESI: m/z 463.2 (M+Na$^+$).

Example 39

N-[2-(2-Methyl-5-(4-(methylsulphonyl)phenyl)-1-phenyl-1H-pyrrol-3-yl)ethyl]-3-propyl urea

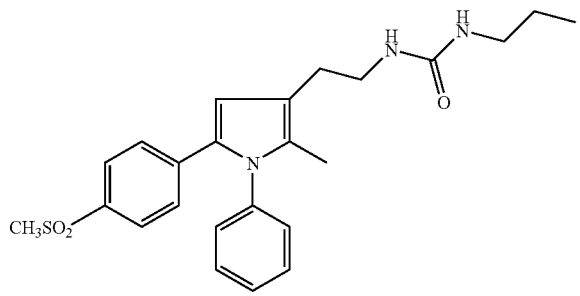

To a suspension of 2-[2-methyl-5-(4-(methylsulphonyl)phenyl)-1-phenyl-1H-pyrrol-3-yl]ethylamine (0.12 mmol) in dry $CH_2Cl_2$ (5 mL), 1,1-carbonyldiimidazole (0.18 mmol) was added at 0° C. and the mixture stirred for 4 h at r.t. The solvent was removed in vacuo and the respective activated amine was obtained. To a stirred solution of activate amine in $CH_3CN$ (6 mL), n-propylamine (0.36 mmol) and DMAP (0.36 mmol) were added at r.t. and the solution was stirred for 18 h. The reaction was hydrolysed with a saturated solution of $NaHCO_3$ and extracted with $CH_2Cl_2$. The organic layers were dried with $Na_2SO_4$ and evaporated to dryness in vacuo. The residue, purified by flash-chromatography (EtOAc), gave the expected compound as a white solid (yield 70%), Mp 157-160 C.°. $^1$H-NMR (CDCl$_3$) δ ppm: 0.87 (t, 3H, J=7.4), 1.47 (m, 2H), 2.02 (s, 3H), 2.66 (t, 2H, J=7.0), 2.95 (s, 3H), 3.09 (m, 2H), 3.37 (m, 2H), 4.59 (m, 1H), 4.71 (m, 1H), 6.40 (s, 1H), 7.11 (m, 4H), 7.35-7.38 (m, 3H), 7.60 (m, 2H). MS-ESI: m/z 462.3 (M+Na$^+$).

Description of the Pharmacological Tests (in vitro testing)

Cell culture. The murine monocyte/macrophage J774 cell line was grown in Dulbecco's modified Eagles medium (DMEM) supplemented with 2 mM glutamine, 25 mM Hepes, penicillin (100 u/mL), streptomycin (100 μg/mL), 10% foetal bovine serum (FBS) and 1.2% Na pyruvate (Bio Whittaker, Europe). Cells were plated in 24 well culture plates at a density of 2.5×105 cells/mL or in 10 cm-diameter culture dishes (1×107 cells/10 mL/dish) and allowed to adhere at 37° C. in 5% CO2/95% O2 for 2 h. Immediately before the experiments, the culture medium was replaced by a fresh medium without FBS in order to avoid interference with radioimmunoassay and cells were stimulated as described (Zingarelli et al. Brit. J Pharmacology, 1997, 120, 357-366).

Assessment of COX-1 activity. Cells were pre-treated with the reference standard or the test compounds (0.01-10 μM) for 15 min and further incubated at 37° C. for 30 min with 15 μM arachidonic acid in order to activate the constitutive COX-1. Stock solutions of the reference standard or of the test compounds were prepared in dimethyl sulphoxide, and an equivalent amount of dimethyl sulphoxide was included in control samples. At the end of the incubation the supernatants were collected for the measurement of PGE2 by radioimmunoassay.

Assessment of COX-2 activity. Cells were stimulated for 24 h with E. coli lipopolysaccharide (LPS, 10 μg/mL) to induce COX-2, in the absence or presence of test compounds, at the concentrations previously reported. The supernatants were collected for the measurement of PGE2 by radioimmunoassay.

Analysis. Throughout the time the experiments lasted, triplicate wells were used for the various conditions of treatment. Results are expressed as the mean, for 3 experiments, of the % inhibition of $PGE_2$ production by test compounds with respect to control samples. Data fit was obtained using the sigmoidal dose-response equation (variable slope). The IC50 were calculated by GraphPad Instat program (GraphPad software).

Animals

Male Swiss albino mice (23-25 g) and Sprague Dawley or Wistar rats (150-200 g) were used. The animals were fed a standard laboratory diet and tap water ad libitum and kept at 23±1° C. with a 12 h light/dark cycle, light on at 7 a.m.

Abdominal Constriction Test

Mice were injected i.p. with a 0.6% solution of acetic acid (10 ml/kg), according to Koster et al. Fed. Proc., 1959, 18, 412. The number of stretching movements was counted for 10 min, starting 5 min after acetic acid injection.

Paw Pressure Test

The nociceptive threshold in the rat was determined with an analgesimeter, according to the method described by Leighton et al, G. E.; Br. J. Pharmacol. 1988, 93, 553-560. Threshold pressure was measured before and 30, 60 and 120 min after treatment. An arbitrary cut-off value of 250 g was adopted. In order to induce an inflammatory process in the rat paw carrageenan (0.1 ml, 1%) was administered i.p. 4 h before test.

Carrageenan-induced Paw Edema

Rats paw volumes were measured using a plethysmometer. Rats received the investigated compounds 4 hours after a 0.1-ml injection of 1.0% carrageenan in the right hind paw. Five hours after the injection of carrageenan (i.e. 1 hour after the administration of the investigated compound), the paw volume of the right hind paw was measured and compared with saline/carrageenan-treated controls. Results are reported as maximum percent effect (MPE), see below for detailed explanation.

Zymosan-induced Paw Edema and Hyperalgesia

The interplantar injection of Zymosan-induced mechanical hyperalgesia may be used as a model of inflammatory pain (Meller, Neuropharmacology, 1994, 33, 1471-1478). In this model, typically a male Sprague-Dawely or Wistar rat (200-250 g) receives an interplantar injection of 4 mg/100 μl zymosan into one hind paw. A marked inflammation occurs in this hind paw. Drugs are administered orally for evaluation of efficacy, 30 min. before the inflammatory insult. The hyperalgesia induced by zymosan administration was evaluated using the Randal-Selitto method (Arch. Int. Pharmacodyn., 1957, 111, 409). The quantitation of the analgesic effect is achieved by an analgesimeter, which consist in applying to the inflamed paw an increasing weight (from 130-140 g up to 500 g). The difference in the mechanical pain threshold between the basal value (generally 230-250 g) and the one tolerated by the animals treated with the drug, determined 4 hours after the inflammatory challenge, is defined as mechanical hyperalgesia.

Mechanical hyperalgesia is expressed for the compounds of the invention as maximum percent effect (MPE) which represents the difference (%) in pain threshold between the animals treated with the drug and the controls that received only the vehicle.

Results are reported as MPE (reduction of the nociceptive effect, due to paw loading with increasing weight, in comparison to controls). 100% MPE means that the animal treated with the compound and Zymosan can tolerate the same stimulus (weight) as the control animals which have not received Zymosan treatment. MPE higher than 100% mean that the animal treated with the compound and Zymosan can tolerate stimuli (weight) higher than the control animals, which has not received Zymosan treatment (hypoalgesia).

In vivo anti-inflammatory effect exerted by the compounds of the invention can be assessed in the same Zymosan induced inflammation test described above, by measuring the volume of the oedema induced by the inflammatory agent. The oedema was evaluated as the increase in the volume of the Zymosan injected paw within a time of 0-2 hrs. The measurements of the variation of the oedema volume of the paw were recorded using hydroplethysmometer. Results are expressed as MPE, maximum percent effect, that in this case represents the reduction (%) in the oedema of treated animals in comparison to controls (animals treated with Zymosan, which received only the vehicle).

Pharmaceutical Compositions

Compounds of Formula I can be used in the manufacture of a suitable medication for the therapeutic treatment of COX-2 mediated disorders such as analgesic treatment of pain, treatment of inflammatory diseases such as arthritis (Osteoarthritis and Rheumatoid arthritis), asthma and inflammatory diseases of the inflammatory tract, gastrointestinal inflammatory conditions, COX-2 mediated neurodegenerative diseases, prevention and treatment of cancer, using oral and/or parenteral dosage forms. The present invention provides a method of treating the diseases mentioned above, which comprises administering an effective amount of a compound of Formula I. For all methods of treatment herein discussed for the compounds of Formula I the daily dosage regimen will preferably be from about 0.1 to about 20 mg/Kg of total body weight. It will also be recognised by one of skill in the art that the optimal quantity and spacing of individual dosages of a compound of Formula I will be determined by the nature and extent of the condition being treated. In order to use a compound of Formula I in therapy, it will normally be formulated into a dosage form in accordance with current guidelines and relevant good laboratory and manufacturing practices. This invention, therefore, also relates to a composition suitable for the above disease treatment, containing a pharmaceutically effective amount of a compound of Formula I and its pharmaceutically acceptable carrier or diluent.

The compounds of the invention can be formulated in a wide variety of oral dosage forms, such as capsules, tablets, pills, dispersible granules. Suitable carriers include but are not limited to magnesium carbonate, magnesium stearate, talc, lactose, methylcellulose, sodium carboxymethyl cellulose.

Techniques used to prepare oral formulations are the conventional mixing, granulation and compression or capsules filling. Other forms suitable for oral administration include emulsions, syrups and aqueous solutions. Emulsions can be prepared using emulsifying agents for example lecithin, propylene glycol or sorbitan monooleate. Aqueous solutions can be prepared by dissolving the active component in water and adding suitable colorants, flavours, stabilising agents.

The compounds of the present invention may be formulated for parenteral administration (e.g., by injection or by continuos infusion) and may be presented in unit dose forms, for example in ampoules or pre-filled syringes. The drug product may be prepared using aqueous vehicles solutions and/or oily emulsions.

The invention claimed is:
1. Compound of Formula I:

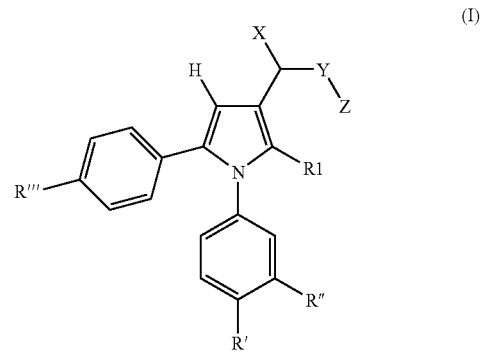

wherein:
the substituent in position 1 of the pyrrole ring is a phenyl, substituted with R' and R" groups, independently selected from: hydrogen, fluorine, chlorine, bromine, methyl, trifluoromethyl, methylsulphonyl and aminosulphonyl ($SO_2NHR_2$), where $R_2$ is defined below, provided that in a compound of formula I, R' and R" are not simultaneously trifluoromethyl, methylsulphonyl, aminosulphonyl;
the substituent R1 in position 2 of the pyrrole ring is methyl, ethyl, isopropyl, n-butyl or isobutyl;
the substituent in the position 3 of the pyrrole ring is a two carbon atoms chain, wherein the groups X, Y, Z have the following meanings:
X is independently selected from: hydrogen, hydroxy (—OH), alkoxy (—$OR_2$), wherein $R_2$ is an alkyl group as defined below;
Y is independently selected from: a carbonyl group (C═O) or a methylene group (—$CH_2$—);
Z is independently selected from: hydroxy (—OH), alkoxy (—$OR_3$), amino (—$NH_2$), alkylamino or arylamino (—$NHR_3$), dialkylamino or alkylarylamino (—$NR_2R_3$), alkylamido or arylamido (—$NHCOR_3$), dialkylamido or alkylarylamido (—$NR_2COR_3$), alkylcarboxyl or arylcarboxyl (—$OCOR_3$), alkyl or aryl carbonate (—O—CO—$OR_3$), alkyl or aryl carbamate (—NH—CO—$OR_3$ or —O—CO—$NR_2R_3$), ureido (—NH—CO—$NHR_3$), wherein $R_2$ and $R_3$ groups are as defined below;
provided that:
when Y is the C═O group and X is H, Z is not hydroxy;
when Y is the C═O group, Z is alkoxy and X is H, $R_3$ is selected from the group consisting of n-propyl, iso-propyl, n-butyl, sec-butyl and iso-butyl;
when Z is selected between alkylamido or arylamido (—$NHCOR_3$), dialkylamido or alkylarylamido (—$NR_2COR_3$), alkylcarboxyl or arylcarboxyl (—$OCOR_3$), alkyl or aryl carbonate (—O—CO—$OR_3$), alkyl or aryl carbamate (—NH—CO—OR$_3$ or —O—CO—NR$_2$R$_3$), ureido (—NH—CO—NHR$_3$), Y is a methylene group;

when Z is selected between amino (—NH$_2$), alkylamino or arylamino (—NHR$_3$), dialkylamino or alkylarylamino (—NR$_2$R$_3$), Y is the CO group;

the group R$_2$ is: methyl, ethyl, n-propyl, isopropyl, n-butyl, sec-butyl or iso-butyl, the group R$_3$ is: hydrogen methyl, ethyl, n-propyl, isopropyl, n-butyl, sec-butyl, iso-butyl, benzyl (—CH$_2$Ar), 1-ethylaryl [—CH(Me)Ar] or aryl (Ar); provided that the R$_3$ group is not hydrogen when the Z group is selected between alkyl or aryl carbonate (—O—CO—OR$_3$) and alkyl or aryl carbamate (NH—CO—OR$_3$); the aryl group (Ar) is phenyl, substituted phenyl, a penta-atomic aromatic heterocycle independently selected from 2-thienyl, 3-thienyl, 2-furyl, 3-furyl, 2-pyrrolyl, 3-pyrrolyl, 3-isoxazolyl; for a substituted phenyl herein is intended a phenyl bearing one or two substituents independently selected from fluorine, chlorine, bromine, cyano, nitro, methyl, trifloromethyl;

the R'" group is independently selected form hydrogen, methylsulphonyl (—SO$_2$Me), and aminosulphonyl (—SO$_2$NHR$_2$), fluorine, chlorine, trifluoromethyl; provided that in each compound of Formula I, only one of the R'" and R' substituent is the methylsulphonyl or the aminosulphonyl and R'" and R' are not simultaneously methylsulphonyl or aminosulphonyl groups;

compounds of Formula I can be chiral compounds, in this case compounds of Formula I can exist as individual enantiomers (S or R) or as mixture of such enantiomers; enantiomers can also exist when Z group is chiral; such enantiomers and their racemic mixtures or enriched mixtures of enantiomers of compounds of Formula I being included; when the X group is not hydrogen, and at the same time the Z group is a chiral, compounds of formula I can exist both as diastereisomers and enantiomers; all the possible diastereoisomers and enantiomers of compounds of Formula I being included.

2. Compounds according to claim 1 of general Formula I, wherein Y is the carbonyl group (C═O), Z is hydroxy (—OH) or alkoxy (—OR$_3$), and X is independently selected from hydroxyl (—OH) and alkoxy (—OR$_2$).

3. Compounds according to claim 1 of general Formula I, wherein Y is the carbonyl group (C═O), Z is amino (—NH$_2$), alkylamino or arylamino (—NHR$_3$), dialkylamino or alkylarylamino (—NR$_2$R$_3$), X is independently selected from hydrogen, hydroxyl (—OH), alkoxy (—OR$_2$), the R$_2$ and R$_3$ groups can be independently selected from the meanings listed in claim 1.

4. Compounds according to claim 1 of general Formula I, wherein Y is the methylene group (—CH$_2$—), Z is independently selected from hydroxy (—OH) and alkoxy (—OR$_3$) groups, X is independently selected from hydrogen, hydroxyl (—OH), alkoxy (—OR$_2$), the R$_3$ and R$_2$ groups can be independently selected from the meanings listed in claim 1.

5. Compounds according to claim 1 of general Formula I, wherein Y is the methylene group (—CH$_2$—), Z is an alkylcarboxyl or an arylcarboxyl (—OCOR$_3$) group, X is independently selected from hydrogen, hydroxyl (—OH), alkoxy (—OR$_2$), the R$_2$ and R$_3$ groups can be independently selected from the meanings listed in claim 1.

6. Compounds according to claim 1 of general Formula I, wherein Y is the methylene group (—CH$_2$—), Z is an amido group (—NH—COR$_3$), X is independently selected from hydrogen, hydroxyl (—OH), alkoxy (—OR$_2$), the R$_2$ and R$_3$ groups can be independently selected from the meanings listed in claim 1.

7. Compounds according to claim 1 of general Formula I, wherein Y is the methylene group (—CH$_2$—), Z is independently selected from the carbamate groups (—O—CO—NHR$_3$) or the carbonates (—O—CO—OR$_3$), X is independently selected from hydrogen, hydroxyl (—OH), alkoxy (—OR$_2$), the R$_2$ and R$_3$ groups can be independently selected from the meanings listed in claim 1.

8. Compounds according to claim 1 of general Formula I, wherein Y is the methylene group (—CH$_2$—), Z is independently selected from the carbamate groups (—NH—CO—OR$_3$) or the urea groups (—NH—CO—NHR$_3$), X is independently selected from hydrogen, hydroxyl (—OH), alkoxy (—OR$_2$), the R$_2$ and R$_3$ groups can be independently selected from the meanings listed in claim 1.

9. A pharmaceutical composition comprising a therapeutically effective amount of a compound of claim 1.

10. A pharmaceutical composition comprising a therapeutically effective amount of a compound of claim 2.

11. A pharmaceutical composition comprising a therapeutically effective amount of a compound of claim 3.

12. A pharmaceutical composition comprising a therapeutically effective amount of a compound of claim 4.

13. A pharmaceutical composition comprising a therapeutically effective amount of a compound of claim 5.

14. A pharmaceutical composition comprising a therapeutically effective amount of a compound of claim 6.

15. A pharmaceutical composition comprising a therapeutically effective amount of a compound of claim 7.

16. A pharmaceutical composition comprising a therapeutically effective amount of a compound of claim 8.

17. Pharmaceutical compositions according to claim 9, further comprising pharmaceutically acceptable inactive ingredients selected from the group which consists of vehicles, binders, flavourings, sweeteners, disaggregants, preservatives, humectants, and mixtures thereof, or ingredients which facilitate transdermal or transmucosal absorption, or which permit the controlled release of the active substance over time.

18. A method for the analgesic treatment in humans of pain comprising the step of administering a therapeutically effective dose of a compound according to claim 1 of general Formula I, to patients in need thereof.

19. A method for the treatment in humans of arthritis pain, postoperative pain, dental pain, muscular pain, and pain resulting from cancer treatment comprising the step of administering a therapeutically effective dose of a compound according to claim 1 of general Formula I, to patients in need thereof.

20. A method for therapeutic treatment in humans of osteoarthritis and rheumatoid arthritis comprising the step of administering a therapeutically effective dose of a compound according to claim 1 of general Formula I to patients in need thereof.

21. A method for the therapeutic treatment of asthma and Chronic Obstructive Pulmonary Disease (COPD), comprising the step of administering a therapeutically effective dose of a compound according to claim 1 of general Formula I, to patients in need thereof.

22. A method for the therapeutic treatment of eczema, psoriasis and dermatitis, comprising the step of administering a therapeutically effective dose of a compound according to claim 1 of general Formula I, to patients in need thereof.

23. A method for the therapeutic treatment of inflammatory bowel disease, ulcerative colitis, Crohn's disease, and post operative inflammatory complications, comprising the step of administering a therapeutically effective dose of a compound according to claim 1 of general Formula I, to patients in need thereof.

24. A method for the therapeutic treatment of Alzheimer's disease, Parkinson's disease, amyotrophic lateral sclerosis, multiple sclerosis, Huntington disease, HIV induced dementia, and head trauma comprising the step of administering a therapeutically effective dose of a compound according to claim 1 of general Formula I, to patients in need thereof.

25. A process for preparing compounds of Formula I, according to claim 2, the process consists in reducing a glyoxylate of Formula II using a reducing agent such as sodiumborohydride in the presence of t-butanol for obtaining compounds of Formula I where X is —OH or in the presence of the appropriate alcohol ($R_3OH$) for obtaining compounds of Formula I where X is —$OR_3$, at a temperature ranging from −30° C. to +60° C.

26. A process for preparing compounds of Formula I, according to claim 3, the process consists in condensing a carboxylic acid of Formula III with ammonia $NH_3$ or the appropriate amine $NH_2R_3$, $NHR_2R_3$, $NHR_3Ar$, $NH_2Ar$ in the presence of an appropriate condensing agent such as carbodiimides (DCC, EDC), with or without a catalyst (HOBT, DMAP), at a temperature ranging from −30° C. to +120° C.

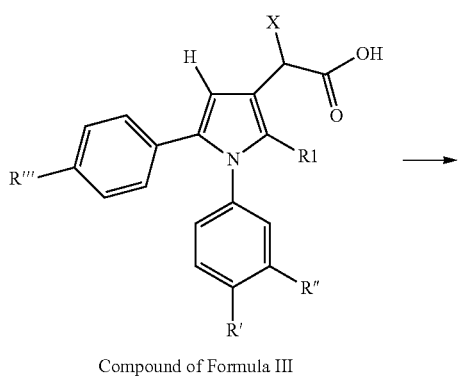

Compound of Formula III

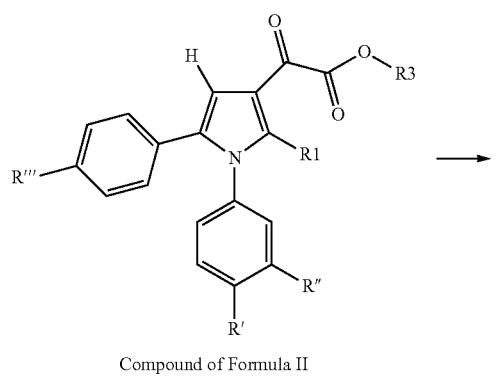

Compound of Formula II

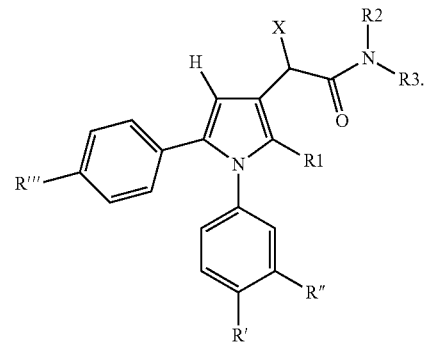

Compound of Formula I

Compound of Formula I

* * * * *